(12) United States Patent
Kawahara

(10) Patent No.: US 11,274,322 B2
(45) Date of Patent: Mar. 15, 2022

(54) METHOD OF PRODUCING LIPID

(71) Applicant: Kao Corporation, Tokyo (JP)

(72) Inventor: Akihito Kawahara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/650,054

(22) PCT Filed: Oct. 3, 2018

(86) PCT No.: PCT/JP2018/036984
§ 371 (c)(1),
(2) Date: Mar. 24, 2020

(87) PCT Pub. No.: WO2019/069969
PCT Pub. Date: Apr. 11, 2019

(65) Prior Publication Data
US 2020/0270650 A1  Aug. 27, 2020

(30) Foreign Application Priority Data

Oct. 6, 2017  (JP) ............................. JP2017-196237

(51) Int. Cl.
*C12P 7/64* (2006.01)
*C12N 9/02* (2006.01)
(Continued)

(52) U.S. Cl.
CPC ................ *C12P 7/64* (2013.01); *C12N 9/18* (2013.01); *C12P 7/6463* (2013.01); *C12Y 203/01041* (2013.01); *Y02E 50/10* (2013.01)

(58) Field of Classification Search
CPC . C12P 7/6436; C12P 7/64; C12N 9/18; C12N 9/1029; Y02E 50/10; C12Y 203/01041; C12Y 203/01015
(Continued)

(56) References Cited

U.S. PATENT DOCUMENTS 5,955,329 A  9/1999  Yuan et al.
2011/0020883 A1  1/2011  Roessler et al.
(Continued)

FOREIGN PATENT DOCUMENTS

WO  WO 92/20236 A1  11/1992
WO  WO 2011/008565 A1  1/2011
WO  WO 2016/014968 A1  1/2016

OTHER PUBLICATIONS

International Search Report (ISR) for PCT/JP2018/036984; I.A. fd Oct. 3, 2018, dated Jan. 8, 2019, from the Japan Patent Office, Tokyo, Japan.
(Continued)

*Primary Examiner* — Robert B Mondesi
*Assistant Examiner* — Mohammad Y Meah
(74) *Attorney, Agent, or Firm* — Sterne, Kessler, Goldstein & Fox P.L.L.C.

(57) ABSTRACT

A method of producing lipids, containing the steps of:
culturing a transformant into which a gene encoding at least one protein selected from the group consisting of the following proteins (A) to (C) is introduced; and
producing fatty acids or lipids containing the same as components:
(A) a protein consisting of an amino acid sequence having at least one amino acid substitution selected from the group consisting of the following (A-1) to (A-11) in the amino acid sequence set forth in SEQ ID NO: 1, and having acyl-ACP thioesterase activity;
(B) a protein consisting of an amino acid sequence having at least one amino acid substitution selected from the group consisting of the following (B-1) to (B-11) in an amino acid sequence having 85% or more identity with the amino acid sequence set forth in SEQ ID NO: 1, and having acyl-ACP thioesterase activity; and
(C) a protein containing the amino acid sequence of the protein (A) or (B), and having acyl-ACP thioesterase activity:
(A-1) substitution of isoleucine for leucine at position 257 of the amino acid sequence set forth in SEQ ID NO: 1;
(A-2) substitution of arginine for threonine at position 251 of the amino acid sequence set forth in SEQ ID NO: 1;
(A-3) substitution of lysine for threonine at position 251 of the amino acid sequence set forth in SEQ ID NO: 1;
(A-4) substitution of histidine for threonine at position 251 of the amino acid sequence set forth in SEQ ID NO: 1;
(A-5) substitution of isoleucine for tryptophan at position 254 of the amino acid sequence set forth in SEQ ID NO: 1;
(A-6) substitution of tyrosine for tryptophan at position 254 of the amino acid sequence set forth in SEQ ID NO: 1;
(A-7) substitution of methionine for leucine at position 257 of the amino acid sequence set forth in SEQ ID NO: 1;
(A-8) substitution of valine for leucine at position 257 of the amino acid sequence set forth in SEQ ID NO: 1;
(A-9) substitution of phenylalanine for leucine at position 257 of the amino acid sequence set forth in SEQ ID NO: 1;
(A-10) substitution of cysteine for valine at position 266 of the amino acid sequence set forth in SEQ ID NO: 1;
(A-11) substitution of tyrosine for tryptophan at position 271 of the amino acid sequence set forth in SEQ ID NO: 1;
(B-1) substitution of isoleucine for an amino acid at a position corresponding to position 257 of the amino acid sequence set forth in SEQ ID NO: 1;
(B-2) substitution of arginine for an amino acid at a position corresponding to position 251 of the amino acid sequence set forth in SEQ ID NO: 1;
(B-3) substitution of lysine for an amino acid at a position corresponding to position 251 of the amino acid sequence set forth in SEQ ID NO: 1;
(Continued)

(B-4) substitution of histidine for an amino acid at a position corresponding to position 251 of the amino acid sequence set forth in SEQ ID NO: 1;
(B-5) substitution of isoleucine for an amino acid at a position corresponding to position 254 of the amino acid sequence set forth in SEQ ID NO: 1;
(B-6) substitution of tyrosine for an amino acid at a position corresponding to position 254 of the amino acid sequence set forth in SEQ ID NO: 1;
(B-7) substitution of methionine for an amino acid at a position corresponding to position 257 of the amino acid sequence set forth in SEQ ID NO: 1;
(B-8) substitution of valine for an amino acid at a position corresponding to position 257 of the amino acid sequence set forth in SEQ ID NO: 1;
(B-9) substitution of phenylalanine for an amino acid at a position corresponding to position 257 of the amino acid sequence set forth in SEQ ID NO: 1;
(B-10) substitution of cysteine for an amino acid at a position corresponding to position 266 of the amino acid sequence set forth in SEQ ID NO: 1; and
(B-11) substitution of tyrosine for an amino acid at a position corresponding to position 271 of the amino acid sequence set forth in SEQ ID NO: 1.

9 Claims, No Drawings

Specification includes a Sequence Listing.

(51) Int. Cl.
  *C12N 9/18* (2006.01)
  *C12P 7/6463* (2022.01)
(58) Field of Classification Search
  USPC .... 435/134, 189, 193, 197, 320.1, 58, 257.2
  See application file for complete search history.

(56) References Cited

U.S. PATENT DOCUMENTS

2015/0247173 A1  9/2015  Kawahara
2016/0355793 A1  12/2016  Nikolau et al.
2017/0114376 A1  4/2017  Ozaki et al.

OTHER PUBLICATIONS

International Preliminary Report on Patentability (IPRP), Chapter I of the Patent Cooperation Treaty, including the Written Opinion, for PCT/JP2018/036984; I.A. fd Oct. 3, 2018 dated Apr. 8, 2020, by the International Bureau of WIPO, Geneva, Switzerland.
Voelker, T.A. et al., "Fatty acid biosynthesis redirected to medium chains in transgenic oilseed plants." Science. 1992;257(5066):72-74. doi: 10.1126/science.1621095.
Deng, M.D. et al., "Ethanol synthesis by genetic engineering in cyanobacteria. Appl Environ Microbiol." 1999;65(2):523-528.
Atsumi, S. et al., "Direct photosynthetic recycling of carbon dioxide to isobutyraldehyde." Nat Biotechnol. 2009;27(12):1177-1180. doi:10.1038/nbt.1586.
Liu, X. et al., "Fatty acid production in genetically modified cyanobacteria." Proc Natl Acad Sci U S A. 2011;108(17):6899-6904. doi:10.1073/pnas.1103014108.

SEQUENCE LISTING

<160> NUMBER OF SEQ ID NOS: 52

<210> SEQ ID NO 1
<211> LENGTH: 355
<212> TYPE: PRT
<213> ORGANISM: Cuphea palustris

<400> SEQUENCE: 1

Met Ala Asn Gly Ser Ala Val Thr Leu Lys Ser Gly Ser Leu Asn Thr
1               5                   10                  15

Gln Glu Asp Thr Leu Ser Ser Ser Pro Pro Arg Ala Phe Phe Asn
            20                  25                  30

Gln Leu Pro Asp Trp Ser Met Leu Leu Thr Ala Ile Thr Thr Val Phe
        35                  40                  45

Val Ala Pro Glu Lys Arg Trp Thr Met Phe Asp Arg Lys Ser Lys Arg
    50                  55                  60

Pro Asn Met Leu Met Asp Ser Phe Gly Leu Glu Arg Val Val Gln Asp

```
            65                  70                  75                  80
        Gly Leu Val Phe Arg Gln Ser Phe Ser Ile Arg Ser Tyr Glu Ile Cys
                        85                  90                  95

Ala Asp Arg Thr Ala Ser Ile Glu Thr Val Met Asn His Val Gln Glu
                    100                 105                 110

Thr Ser Leu Asn Gln Cys Lys Ser Ile Gly Leu Leu Asp Asp Gly Phe
                    115                 120                 125

Gly Arg Ser Pro Glu Met Cys Lys Arg Asp Leu Ile Trp Val Val Thr
                130                 135                 140

Arg Met Lys Ile Met Val Asn Arg Tyr Pro Thr Trp Gly Asp Thr Ile
        145                 150                 155                 160

Glu Val Ser Thr Trp Leu Ser Gln Ser Gly Lys Ile Gly Met Gly Arg
                        165                 170                 175

Asp Trp Leu Ile Ser Asp Cys Asn Thr Gly Glu Ile Leu Val Arg Ala
                    180                 185                 190

Thr Ser Val Tyr Ala Met Met Asn Gln Lys Thr Arg Arg Phe Ser Lys
                    195                 200                 205

Leu Pro His Glu Val Arg Gln Glu Phe Ala Pro His Phe Leu Asp Ser
            210                 215                 220

Pro Pro Ala Ile Glu Asp Asn Asp Gly Lys Leu Gln Lys Phe Asp Val
        225                 230                 235                 240

Lys Thr Gly Asp Ser Ile Arg Lys Gly Leu Thr Pro Gly Trp Tyr Asp
                        245                 250                 255

Leu Asp Val Asn Gln His Val Ser Asn Val Lys Tyr Ile Gly Trp Ile
                    260                 265                 270

Leu Glu Ser Met Pro Thr Glu Val Leu Glu Thr Gln Glu Leu Cys Ser
                    275                 280                 285

Leu Thr Leu Glu Tyr Arg Arg Glu Cys Gly Arg Asp Ser Val Leu Glu
                290                 295                 300

Ser Val Thr Ser Met Asp Pro Ser Lys Val Gly Asp Arg Phe Gln Tyr
        305                 310                 315                 320

Arg His Leu Leu Arg Leu Glu Asp Gly Ala Asp Ile Met Lys Gly Arg
                        325                 330                 335

Thr Glu Trp Arg Pro Lys Asn Ala Gly Thr Asn Gly Ala Ile Ser Thr
                    340                 345                 350

Gly Lys Thr
                355

<210> SEQ ID NO 2
<211> LENGTH: 1068
<212> TYPE: DNA
<213> ORGANISM: Cuphea palustris

<400> SEQUENCE: 2
atggctaacg gttctgcagt aactctaaag tctggcagcc tcaacactca ggaggacact       60
ttgtcgtcgt cccctcctcc ccgggctttt tttaaccagt gcctgattg  gagtatgctt     120 ctgactgcaa tcacaaccgt cttcgtggca ccagagaagc ggtggactat gtttgatagg      180
aaatctaaga ggcctaacat gctcatggac tcgtttgggt tggagagagt tgttcaggat      240
gggctcgtgt tcagacagag ttttttcgatt aggtcttatg aaatatgcgc tgatcgaaca     300
gcctctatag agacggtgat gaaccacgtc caggaaacat cactcaatca atgtaagagt      360
ataggtcttc tcgatgacgg ctttggtcgt agtcctgaga tgtgtaaaag ggacctcatt      420
tgggtggtta caagaatgaa gataatggtg aatcgctatc caacttgggg cgatactatc      480
```

```
gaggtcagta cctggctctc tcaatcgggg aaaatcggta tgggtcgcga ttggctaata    540
agtgattgca acacaggaga aattcttgta agagcaacga gtgtgtatgc catgatgaat    600
caaaagacga gaagattctc aaaactccca cacgaggttc gccaggaatt tgcgcctcat    660
tttctggact ctcctcctgc cattgaagac aacgacggta aattgcagaa gtttgatgtg    720
aagactggtg attccattcg caagggtcta actccggggt ggtatgactt ggatgtcaat    780
cagcacgtaa gcaacgtgaa gtacattggg tggattctcg agagtatgcc aacgaaagtt    840
ttggagactc aggagctatg ttctctcacc cttgaatata ggcgggaatg cggaagggac    900
agtgtgctgg agtccgtgac ctctatggat ccctcaaaag ttggagaccg gtttcagtac    960
cggcaccttc tgcggcttga ggatgggggct gatatcatga agggaagaac tgagtggcgg   1020
ccgaagaatg caggaactaa cggggcgata tcaacaggaa agacttga                 1068
```

<210> SEQ ID NO 3
<211> LENGTH: 25
<212> TYPE: DNA
<213> ORGANISM: Artificial Sequence
<220> FEATURE:
<223> OTHER INFORMATION: Primer pBS-F

<400> SEQUENCE: 3
gcgttaatat tttgttaaaa ttcgc    25

<210> SEQ ID NO 4
<211> LENGTH: 22
<212> TYPE: DNA
<213> ORGANISM: Artificial Sequence
<220> FEATURE:
<223> OTHER INFORMATION: Primer pBS-R

<400> SEQUENCE: 4
agctgtttcc tgtgtgaaat tg    22

<210> SEQ ID NO 5
<211> LENGTH: 38
<212> TYPE: DNA
<213> ORGANISM: Artificial Sequence
<220> FEATURE:
<223> OTHER INFORMATION: Primer pBS/CpTE-F

<400> SEQUENCE: 5
acacaggaaa cagctatggc taacggttct gcagtaac    38

<210> SEQ ID NO 6
<211> LENGTH: 40
<212> TYPE: DNA
<213> ORGANISM: Artificial Sequence
<220> FEATURE:
<223> OTHER INFORMATION: Primer CpTE/pBS-R

<400> SEQUENCE: 6
acaaaatatt aacgctcaag tctttcctgt tgatatcgcc    40

<210> SEQ ID NO 7
<211> LENGTH: 24
<212> TYPE: DNA
<213> ORGANISM: Artificial Sequence
<220> FEATURE:
<223> OTHER INFORMATION: Primer CpTE_T251-R

<400> SEQUENCE: 7
tagacccttg cgaatggaat cacc        24

<210> SEQ ID NO 8
<211> LENGTH: 35
<212> TYPE: DNA
<213> ORGANISM: Artificial Sequence
<220> FEATURE:
<223> OTHER INFORMATION: Primer CpTE_T251R-F

<400> SEQUENCE: 8
attcgcaagg gtctacgtcc ggggtggtat gactt        35

<210> SEQ ID NO 9
<211> LENGTH: 35
<212> TYPE: DNA
<213> ORGANISM: Artificial Sequence
<220> FEATURE:
<223> OTHER INFORMATION: Primer CpTE_T251K-F

<400> SEQUENCE: 9
attcgcaagg gtctaaaacc ggggtggtat gactt        35

<210> SEQ ID NO 10
<211> LENGTH: 35
<212> TYPE: DNA
<213> ORGANISM: Artificial Sequence
<220> FEATURE:
<223> OTHER INFORMATION: Primer CpTE_T251H-F

<400> SEQUENCE: 10
attcgcaagg gtctacatcc ggggtggtat gactt        35

<210> SEQ ID NO 11
<211> LENGTH: 21
<212> TYPE: DNA
<213> ORGANISM: Artificial Sequence
<220> FEATURE:
<223> OTHER INFORMATION: Primer CpTE_W254-R

<400> SEQUENCE: 11
ccccggagtt agacccttgc g        21

<210> SEQ ID NO 12
<211> LENGTH: 35
<212> TYPE: DNA
<213> ORGANISM: Artificial Sequence
<220> FEATURE:
<223> OTHER INFORMATION: Primer CpTE_W254I-F

<400> SEQUENCE: 12
ggtctaactc cggggattta tgacttggat gtcaa        35

<210> SEQ ID NO 13
<211> LENGTH: 35
<212> TYPE: DNA
<213> ORGANISM: Artificial Sequence
<220> FEATURE:
<223> OTHER INFORMATION: Primer CpTE_W254Y-F

<400> SEQUENCE: 13
ggtctaactc cggggtatta tgacttggat gtcaa        35

<210> SEQ ID NO 14
<211> LENGTH: 23
<212> TYPE: DNA
<213> ORGANISM: Artificial Sequence

```
<220> FEATURE:
<223> OTHER INFORMATION: Primer CpTE_L257-R

<400> SEQUENCE: 14
gtcataccac cccggagtta gac                                          23

<210> SEQ ID NO 15
<211> LENGTH: 35
<212> TYPE: DNA
<213> ORGANISM: Artificial Sequence
<220> FEATURE:
<223> OTHER INFORMATION: Primer CpTE_L257I-F

<400> SEQUENCE: 15
ccggggtggt atgacattga tgtcaatcag cacgt                             35

<210> SEQ ID NO 16
<211> LENGTH: 35
<212> TYPE: DNA
<213> ORGANISM: Artificial Sequence
<220> FEATURE:
<223> OTHER INFORMATION: Primer CpTE_L257M-F

<400> SEQUENCE: 16
ccggggtggt atgacatgga tgtcaatcag cacgt                             35

<210> SEQ ID NO 17
<211> LENGTH: 35
<212> TYPE: DNA
<213> ORGANISM: Artificial Sequence
<220> FEATURE:
<223> OTHER INFORMATION: Primer CpTE_L257V-F

<400> SEQUENCE: 17
ccggggtggt atgacgttga tgtcaatcag cacgt                             35

<210> SEQ ID NO 18
<211> LENGTH: 35
<212> TYPE: DNA
<213> ORGANISM: Artificial Sequence
<220> FEATURE:
<223> OTHER INFORMATION: Primer CpTE_L257F-F

<400> SEQUENCE: 18
ccggggtggt atgactttga tgtcaatcag cacgt                             35

<210> SEQ ID NO 19
<211> LENGTH: 25
<212> TYPE: DNA
<213> ORGANISM: Artificial Sequence
<220> FEATURE:
<223> OTHER INFORMATION: Primer CpTE_V266-R

<400> SEQUENCE: 19
gttgcttacg tgctgattga catcc                                        25

<210> SEQ ID NO 20
<211> LENGTH: 35
<212> TYPE: DNA
<213> ORGANISM: Artificial Sequence
<220> FEATURE:
<223> OTHER INFORMATION: Primer CpTE_V266C-F

<400> SEQUENCE: 20
cagcacgtaa gcaactgtaa gtacattggg tggat                             35
```

<210> SEQ ID NO 21
<211> LENGTH: 25
<212> TYPE: DNA
<213> ORGANISM: Artificial Sequence
<220> FEATURE:
<223> OTHER INFORMATION: Primer CpTE_W271-R

<400> SEQUENCE: 21
cccaatgtac ttcacgttgc ttacg                                    25

<210> SEQ ID NO 22
<211> LENGTH: 35
<212> TYPE: DNA
<213> ORGANISM: Artificial Sequence
<220> FEATURE:
<223> OTHER INFORMATION: Primer CpTE_W271Y-F

<400> SEQUENCE: 22
gtgaagtaca ttgggtatat tctcgagagt atgcc                         35

<210> SEQ ID NO 23
<211> LENGTH: 24
<212> TYPE: DNA
<213> ORGANISM: Artificial Sequence
<220> FEATURE:
<223> OTHER INFORMATION: Primer CpTE_V106-R

<400> SEQUENCE: 23
cgtctctata gaggctgttc gatc                                     24

<210> SEQ ID NO 24
<211> LENGTH: 35
<212> TYPE: DNA
<213> ORGANISM: Artificial Sequence
<220> FEATURE:
<223> OTHER INFORMATION: Primer CpTE_V106I-F

<400> SEQUENCE: 24
gcctctatag agacgattat gaaccacgtc cagga                         35

<210> SEQ ID NO 25
<211> LENGTH: 23
<212> TYPE: DNA
<213> ORGANISM: Artificial Sequence
<220> FEATURE:
<223> OTHER INFORMATION: Primer CpTE_N108-R

<400> SEQUENCE: 25
catcaccgtc tctatagagg ctg                                      23

<210> SEQ ID NO 26
<211> LENGTH: 35
<212> TYPE: DNA
<213> ORGANISM: Artificial Sequence
<220> FEATURE:
<223> OTHER INFORMATION: Primer CpTE_N108R-F

<400> SEQUENCE: 26
atagagacgg tgatgcgtca cgtccaggaa acatc                         35

<210> SEQ ID NO 27
<211> LENGTH: 35
<212> TYPE: DNA
<213> ORGANISM: Artificial Sequence
<220> FEATURE:
<223> OTHER INFORMATION: Primer CpTE_N108K-F

<400> SEQUENCE: 27
atagagacgg tgatgaaaca cgtccaggaa acatc                35

<210> SEQ ID NO 28
<211> LENGTH: 25
<212> TYPE: DNA
<213> ORGANISM: Artificial Sequence
<220> FEATURE:
<223> OTHER INFORMATION: Primer CpTE_V110-R

<400> SEQUENCE: 28
gtggttcatc accgtctcta tagag                25

<210> SEQ ID NO 29
<211> LENGTH: 35
<212> TYPE: DNA
<213> ORGANISM: Artificial Sequence
<220> FEATURE:
<223> OTHER INFORMATION: Primer CpTE_V110I-F

<400> SEQUENCE: 29
acggtgatga accacattca ggaaacatca ctcaa                35

<210> SEQ ID NO 30
<211> LENGTH: 35
<212> TYPE: DNA
<213> ORGANISM: Artificial Sequence
<220> FEATURE:
<223> OTHER INFORMATION: Primer CpTE_V110M-F

<400> SEQUENCE: 30
acggtgatga accacatgca ggaaacatca ctcaa                35

<210> SEQ ID NO 31
<211> LENGTH: 35
<212> TYPE: DNA
<213> ORGANISM: Artificial Sequence
<220> FEATURE:
<223> OTHER INFORMATION: Primer CpTE_V110L-F

<400> SEQUENCE: 31
acggtgatga accacttaca ggaaacatca ctcaa                35

<210> SEQ ID NO 32
<211> LENGTH: 35
<212> TYPE: DNA
<213> ORGANISM: Artificial Sequence
<220> FEATURE:
<223> OTHER INFORMATION: Primer CpTE_V110F-F

<400> SEQUENCE: 32
acggtgatga accactttca ggaaacatca ctcaa                35

<210> SEQ ID NO 33
<211> LENGTH: 25
<212> TYPE: DNA
<213> ORGANISM: Artificial Sequence
<220> FEATURE:
<223> OTHER INFORMATION: Primer CpTE_C118-R

<400> SEQUENCE: 33
ttgattgagt gatgtttcct ggacg                25

<210> SEQ ID NO 34

```
<211> LENGTH: 35
<212> TYPE: DNA
<213> ORGANISM: Artificial Sequence
<220> FEATURE:
<223> OTHER INFORMATION: Primer CpTE_C118I-F

<400> SEQUENCE: 34
acatcactca atcaaattaa gagtataggt cttct                              35

<210> SEQ ID NO 35
<211> LENGTH: 26
<212> TYPE: DNA
<213> ORGANISM: Artificial Sequence
<220> FEATURE:
<223> OTHER INFORMATION: Primer CpTE_M174-R

<400> SEQUENCE: 35
accgattttc cccgattgag agagcc                                       26

<210> SEQ ID NO 36
<211> LENGTH: 35
<212> TYPE: DNA
<213> ORGANISM: Artificial Sequence
<220> FEATURE:
<223> OTHER INFORMATION: Primer CpTE_M174I-F

<400> SEQUENCE: 36
tcggggaaaa tcggtattgg tcgcgattgg ctaat                             35

<210> SEQ ID NO 37
<211> LENGTH: 37
<212> TYPE: DNA
<213> ORGANISM: Artificial Sequence
<220> FEATURE:
<223> OTHER INFORMATION: Primer pUC118/0918up-F

<400> SEQUENCE: 37
ggatcctcta gagtcagctc cgttgtcgca gtgtcag                           37

<210> SEQ ID NO 38
<211> LENGTH: 38
<212> TYPE: DNA
<213> ORGANISM: Artificial Sequence
<220> FEATURE:
<223> OTHER INFORMATION: Primer 0918down/pUC118-R

<400> SEQUENCE: 38
gcatgcctgc aggtcagaca tcactcaagt catcagtc                          38

<210> SEQ ID NO 39
<211> LENGTH: 32
<212> TYPE: DNA
<213> ORGANISM: Artificial Sequence
<220> FEATURE:
<223> OTHER INFORMATION: Primer 0918up/spr-F

<400> SEQUENCE: 39
tcgggcacca caggcatcga ttttcgttcg tg                                32

<210> SEQ ID NO 40
<211> LENGTH: 34
<212> TYPE: DNA
<213> ORGANISM: Artificial Sequence
<220> FEATURE:
<223> OTHER INFORMATION: Primer spr/0918down-R

<400> SEQUENCE: 40
```

-continued aatcggctgg ggttccatat gcaagggttt attg                              34

<210> SEQ ID NO 41
<211> LENGTH: 22
<212> TYPE: DNA
<213> ORGANISM: Artificial Sequence
<220> FEATURE:
<223> OTHER INFORMATION: Primer 0918up-R

<400> SEQUENCE: 41
gcctgtggtg cccgaggtat ag                                           22

<210> SEQ ID NO 42
<211> LENGTH: 22
<212> TYPE: DNA
<213> ORGANISM: Artificial Sequence
<220> FEATURE:
<223> OTHER INFORMATION: Primer 0918down-F

<400> SEQUENCE: 42 gaacccccagc cgattgaaga tg                                          22

<210> SEQ ID NO 43
<211> LENGTH: 17
<212> TYPE: DNA
<213> ORGANISM: Artificial Sequence
<220> FEATURE:
<223> OTHER INFORMATION: Primer Sp-F

<400> SEQUENCE: 43
atcgattttc gttcgtg                                                 17

<210> SEQ ID NO 44
<211> LENGTH: 38
<212> TYPE: DNA
<213> ORGANISM: Artificial Sequence
<220> FEATURE:
<223> OTHER INFORMATION: Primer 0918up/Ptrc-F

<400> SEQUENCE: 44
tcgggcacca caggcttgac aattaatcat ccggctcg                          38

<210> SEQ ID NO 45
<211> LENGTH: 23
<212> TYPE: DNA
<213> ORGANISM: Artificial Sequence
<220> FEATURE:
<223> OTHER INFORMATION: Primer Ptrc-R

<400> SEQUENCE: 45
ggtctgtttc ctgtgtgaaa ttg                                          23

<210> SEQ ID NO 46
<211> LENGTH: 38
<212> TYPE: DNA
<213> ORGANISM: Artificial Sequence
<220> FEATURE:
<223> OTHER INFORMATION: Primer Ptrc/CpTE-F

<400> SEQUENCE: 46
cacaggaaac agaccatggc taacggttct gcagtaac                          38

<210> SEQ ID NO 47
<211> LENGTH: 40
<212> TYPE: DNA

<213> ORGANISM: Artificial Sequence
<220> FEATURE:
<223> OTHER INFORMATION: Primer CpTE/spr-R

<400> SEQUENCE: 47
cgaacgaaaa tcgattcaag tctttcctgt tgatatcgcc     40

<210> SEQ ID NO 48
<211> LENGTH: 411
<212> TYPE: PRT
<213> ORGANISM: Cuphea palustris

<400> SEQUENCE: 48

```
Met Val Ala Ala Ala Ser Ser Ala Cys Phe Pro Val Pro Ser Pro
1               5                   10                  15

Gly Ala Ser Pro Lys Pro Gly Lys Leu Gly Asn Trp Ser Ser Leu
                20                  25                  30

Ser Pro Ser Leu Lys Pro Lys Ser Ile Pro Asn Gly Gly Phe Gln Val
        35                  40                  45

Lys Ala Asn Ala Ser Ala His Pro Lys Ala Asn Gly Ser Ala Val Thr
    50                  55                  60

Leu Lys Ser Gly Ser Leu Asn Thr Gln Glu Asp Thr Leu Ser Ser Ser
65                  70                  75                  80

Pro Pro Pro Arg Ala Phe Phe Asn Gln Leu Pro Asp Trp Ser Met Leu
                85                  90                  95

Leu Thr Ala Ile Thr Thr Val Phe Val Ala Pro Glu Lys Arg Trp Thr
                100                 105                 110

Met Phe Asp Arg Lys Ser Lys Arg Pro Asn Met Leu Met Asp Ser Phe
            115                 120                 125

Gly Leu Glu Arg Val Val Gln Asp Gly Leu Val Phe Arg Gln Ser Phe
        130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
                180                 185                 190

Arg Asp Leu Ile Trp Val Val Thr Arg Met Lys Ile Met Val Asn Arg
            195                 200                 205

Tyr Pro Thr Trp Gly Asp Thr Ile Glu Val Ser Thr Trp Leu Ser Gln
        210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
                260                 265                 270

Phe Ala Pro His Phe Leu Asp Ser Pro Ala Ile Glu Asp Asn Asp
            275                 280                 285

Gly Lys Leu Gln Lys Phe Asp Val Lys Thr Gly Asp Ser Ile Arg Lys
        290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335
```

Leu Glu Thr Gln Glu Leu Cys Ser Leu Thr Leu Glu Tyr Arg Arg Glu
                340                 345                 350

Cys Gly Arg Asp Ser Val Leu Glu Ser Val Thr Ser Met Asp Pro Ser
            355                 360                 365

Lys Val Gly Asp Arg Phe Gln Tyr Arg His Leu Leu Arg Leu Glu Asp
        370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
                405                 410

<210> SEQ ID NO 49
<211> LENGTH: 1236
<212> TYPE: DNA
<213> ORGANISM: Cuphea palustris

<400> SEQUENCE: 49

```
atggtggctg ctgcagcaag ttctgcatgc ttccctgttc catccccagg agcctcccct      60
aaacctggga agttaggcaa ctggtcatcg agtttgagcc cttccttgaa gcccaagtca     120
atccccaatg gcggatttca ggttaaggca atgccagtg cgcatcctaa ggctaacggt      180
tctgcagtaa ctctaaagtc tggcagcctc aacactcagg aggacacttt gtcgtcgtcc    240
cctcctcccc gggctttttt taaccagttg cctgattgga gtatgcttct gactgcaatc    300
acaaccgtct tcgtggcacc agagaagcgg tggactatgt ttgataggaa atctaagagg   360
cctaacatgc tcatggactc gtttgggttg gagagagttg ttcaggatgg gctcgtgttc   420
agacagagtt tttcgattag gtcttatgaa atatgcgctg atcgaacagc ctctatagag   480
acggtgatga accacgtcca ggaaacatca ctcaatcaat gtaagagtat aggtcttctc   540
gatgacggct ttggtcgtag tcctgagatg tgtaaaaggg acctcatttg gtggttaca    600
agaatgaaga taatggtgaa tcgctatcca acttggggcg atactatcga ggtcagtacc   660
tggctctctc aatcggggaa aatcggtatg ggtcgcgatt ggctaataag tgattgcaac   720
acaggagaaa ttcttgtaag agcaacgagt gtgtatgcca tgatgaatca aaagacgaga   780
agattctcaa aactcccaca cgaggttcgc aggaatttg cgcctcattt tctggactct    840
cctcctgcca ttgaagacaa cgacggtaaa ttgcagaagt tgatgtgaa gactggtgat    900
tccattcgca agggtctaac tccggggtgg tatgacttgg atgtcaatca gcacgtaagc   960
aacgtgaagt acattgggtg gattctcgag agtatgccaa cagaagtttt ggagactcag  1020
gagctatgtt ctctcaccct tgaatatagg cgggaatgcg gaagggacag tgtgctggag  1080
tccgtgacct ctatggatcc ctcaaaagtt ggagaccggt ttcagtaccg gcaccttctg  1140
cggcttgagg atgggctga tatcatgaag ggaagaactg agtggcggcc gaagaatgca  1200
ggaactaacg ggcgatatc aacaggaaag acttga                             1236
```

<210> SEQ ID NO 50
<211> LENGTH: 2864
<212> TYPE: DNA
<213> ORGANISM: Synechococcus elongatus

<400> SEQUENCE: 50

```
agctccgttg tcgcagtgtc agaactcatg ctagcgctc ctcctgaggg ccacacaaag       60
gtgttgatct cactctaggg ggattgggcc gttcctggga atcagtcttg tactacggtt    120
tgtttcaacc gcgatcgcca gccagtttag gccgccgagc cagggcaacg ggcatctgac   180
```

```
agcgctgctt gactcacaag aacttgagcc aggctgagac gagcgatcgc ccagtcgcaa    240
aactcccata agcaatgcag ggaatgcgtg atcggtctct aaaatgagga cgctggctga    300
ggagagtaga ccgagtgact ggaaccgccc tcgcgcaacc ccgcgccatt acgcccacg     360 aacagcagct tttggccaaa ctgaaaagct atcgcgatat ccaaagcttg tcgcaaattt    420
ggggacgtgc tgccagtcaa tttggatcga tgccggcttt ggttgcaccc catgccaaac    480
cagcgatcac cctcagttat caagaattgg cgattcagat ccaagcgttt gcagccggac    540
tgctcgcgct gggagtgcct acctccacag ccgatgactt tccgcctcgc ttggcgcagt    600
ttgcggataa cagcccccgc tggttgattg ctgaccaagg cacgttgctg cagggggctg    660
ccaatgcggt gcgcggcgcc caagctgaag tatcggagct gctctacgtc ttagaggaca    720
gcggttcgat cggcttgatt gtcgaagacg cggcgctgct gaagaaacta cagcctggtt    780
tagcgtcact atcgctgcag tttgtgatcg tgctcagcga tgaagtagtc gagatcgaca    840
gcctgcgcgt cgttggtttt agtgacgtgc tggagatggg gcgatcgctg ccggcaccgg    900
agccaatttt gcagctcgat cgcttagcca ctttgatcta tacctcgggc accacaggcc    960
caccgaaggg cgtgatgctt tctcacggca acctgctgca ccaagtcaca acattaggtg   1020
tggttgtgca gccgcaacct ggcgacaccg tgctgagtat tttgccgact tggcactcct   1080
acgagcgagc ttgtgaatat ttcctgctct cccagggctg cacacaggtc tacgacgcgc   1140
tgcgcaatgt caaacaagac atccggcagt atcggccgca gttcatggtc agtgtgctgc   1200
gcctctggga atcgatctac gagggcgtgc agaagcagtt tcgcgagcaa ccggcgaaga   1260
aacgtcgctt gatcgatacc ttctttggct tgagtcaacg ctatgttttg gcacggcgcc   1320
gctggcaagg actggatttg ctggcactga accaatcccc agcccagcgc ctcgctgagg   1380
gtgtccggat gttggcgcta gcaccgttgc ataagctggg cgatcgcctc gtctacggca   1440
aagtacgaga agccacgggt ggccgaattc ggcaggtgat cagtggcggt ggctcactgg   1500
cactgcacct cgataccttc ttcgaaattg ttggtgttga tttgctggtg ggttatggct   1560
tgacagaaac ctcaccagtg ctgacggggc gacggccttg gcacaaccta cggggttcgg   1620
ccggtcagcc gattccaggt acggcgattc ggatcgtcga tcctgaaacg aaggaaaacc   1680
gacccagtgg cgatcgcggc ttggtgctgg cgaaagggcc gcaaatcatg cagggctact   1740
tcaataaacc cgaggcgacc gcgaaagcga tcgatgccga aggttggttt gacaccggcg   1800
acttaggcta catcgtcggt gaaggcaact tggtgctaac ggggcgcgct aaggacacga   1860
tcgtgctgac caatggcgaa aacattgaac cccagccgat tgaagatgcc tgcctacgaa   1920
gttcctatat cagccaaatc atgttggtgg acaagaccg  caagagtttg ggggcgttga   1980
ttgtgcccaa tcaagaggcg atcgcactct gggccagcga acaggcatc  agccaaaccg   2040 atctgcaggg agtggtacag aagctgattc gcgaggaact gaaccgcgaa gtgcgcgatc   2100
gcccgggcta ccgcatcgac gatcgcattg gaccattccg cctcatcgaa gaaccgttca   2160
gcatggaaaa tggccagcta acccaaaccc tgaaaatccg tcgcaacgtt gtcgcggaac   2220
actacgcggc tatgatcgac gggatgtttg aatcggcgag ttaagtgtcg attcagcacc   2280
ttgacccttc attctttcct gtgacccata ctatgaccct cggtactcct ctgcagctaa   2340
agcggacgat caatgtcaaa gcgatcgtga cgccgacttg gaagcaagaa gcccaaaatg   2400
cactgcaggg ccagctcggt caagtggatg cgcagattca acagttggat ttgcagggc   2460 aagcagcaat caacgaaatt cgcagccaaa gtgccaatcc agtgcatccg aatgtgttgc   2520
aacagattga caacattcag attcaagtca atcagcaaaa aacgcagctg cttgagcaga   2580
```

| agaatcaaat tctccagcaa ctgcaacaag tacaaacggt caacttagaa gaagaagtca | 2640 |
| accaaggtca aattgagagc ttctttgagc tgcatccggg cgataacttg attgaaaaaa | 2700 |
| tgcaagttga atcgtgctg cgcgatggtg ttgttgttga gattcgcggt aatgcttagg | 2760 |
| ttttcttgac tcgaccatca atttgtgttg atagctcaca aaaagtttgt gggcttttt | 2820 |
| catgcccgtt aagaatactg tgactgatga cttgagtgat gtct | 2864 |

<210> SEQ ID NO 51
<211> LENGTH: 1158
<212> TYPE: DNA
<213> ORGANISM: Artificial Sequence
<220> FEATURE:
<223> OTHER INFORMATION: spectinomycin resistance gene

<400> SEQUENCE: 51

| atcgattttc gttcgtgaat acatgttata taactataa ctaataacgt aacgtgactg | 60 |
| gcaagagata ttttaaaac aatgaatagg tttacactta ctttagtttt atggaaatga | 120 |
| aagatcatat catatataat ctagaataaa attaactaaa ataattatta tctagataaa | 180 |
| aaatttagaa gccaatgaaa tctataaata aactaaatta agtttattta attaacaact | 240 |
| atggatataa ataggtact aatcaaaata gtgaggagga tatatttgaa tacatacgaa | 300 |
| caaattaata aagtgaaaaa aatacttcgg aaacatttaa aaaataaccct tattggtact | 360 |
| tacatgtttg gatcaggagt tgagagtgga ctaaaaccaa atagtgatct tgactttta | 420 |
| gtcgtcgtat ctgaaccatt gacagatcaa agtaaagaaa tacttataca aaaaattaga | 480 |
| cctatttcaa aaaaaatagg agataaaagc aacttacgat atattgaatt aacaattatt | 540 |
| attcagcaag aaatggtacc gtggaatcat cctcccaaac aagaatttat ttatggagaa | 600 |
| tggttacaag agctttatga acaaggatac attcctcaga aggaattaaa ttcagattta | 660 |
| accataatgc tttaccaagc aaaacgaaaa aataaaagaa tatacggaaa ttatgactta | 720 |
| gaggaattac tacctgatat tccattttct gatgtgagaa gagccattat ggattcgtca | 780 |
| gaggaattaa tagataatta tcaggatgat gaaaccaact ctatattaac tttatgccgt | 840 |
| atgattttaa ctatggacac gggtaaaatc ataccaaaag atattgcggg aaatgcagtg | 900 |
| gctgaatctt ctccattaga acataggag agaattttgt tagcagttcg tagttatctt | 960 |
| ggagagaata ttgaatggac taatgaaaat gtaaatttaa ctataaacta tttaaataac | 1020 |
| agattaaaaa aattataaaa aaattgaaaa aatggtggaa acacttttt caatttttt | 1080 |
| gttttattat ttaatatttg ggaaatattc attctaattg gtaatcagat tttagaaaac | 1140 |
| aataaaccct tgcatatg | 1158 |

<210> SEQ ID NO 52
<211> LENGTH: 74
<212> TYPE: DNA
<213> ORGANISM: Artificial Sequence
<220> FEATURE:
<223> OTHER INFORMATION: trc promoter

<400> SEQUENCE: 52

| ttgacaatta atcatccggc tcgtataatg tgtggaattg tgagcggata acaatttcac | 60 |
| acaggaaaca gacc | 74 |

METHOD OF PRODUCING LIPID

TECHNICAL FIELD

The present invention relates to a method of producing a lipid.

Further, the present invention relates to an acyl-ACP thioesterase variant, a gene encoding the same, and a transformant obtained by introducing the gene, for use in this method.

BACKGROUND ART

Fatty acids are one of the principal components of lipids. In vivo, fatty acids are bonded to glycerin via an ester bond to form lipids (fat and oil) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkylbenzenesulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary amine salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, fats and oils derived from plants are also used as raw materials of biodiesel fuels.

Moreover, a medium-chain fatty acid having 8 or 10 carbon atoms is used for health food or an etching agent. Moreover, alcohol derivatives that are obtained by reducing the medium-chain fatty acid having 8 or 10 carbon atoms are also used as industrial raw materials such as cosmetics, surfactants and plasticizers.

Fatty acids and lipids are widely used for various applications shown above. Therefore, it has been attempted to enhance the productivity of fatty acids or lipids in vivo by using plants and the like. Furthermore, the applications and usefulness of fatty acids depend on the number of carbon atoms therein. Therefore, controlling of the number of carbon atoms of the fatty acids, namely, a chain length thereof has also been attempted.

For example, a method of accumulating fatty acids having 12 carbon atoms by introducing a gene encoding an acyl-ACP (acyl carrier protein) thioesterase (hereinafter, also merely referred to as "TE") derived from *Umbellularia californica* (California bay) into a host (Patent Literature 1, and Non-Patent Literature 1) has been proposed.

Moreover, it is known that the productivity of medium-chain fatty acids having 8 or 10 carbon atoms in a transformant obtained is improved by introducing a gene encoding a TE derived from plants belonging to the genus *Cuphea*, such as *Cuphea palustris* and *Cuphea hookeriana* into a host. Moreover, Patent Literatures 2 and 3 disclose TE variants in which specific amino acids are replaced at the 172nd to 221st sites or sites corresponding thereto in an amino acid sequence (SEQ ID NO: 1) obtained by deleting a signal sequence on N-terminal side from a wild-type TE derived from *Cuphea palustris* consisting of the amino acid sequence set forth in SEQ ID NO: 48 or in an amino acid sequence having high identity with the amino acid sequence set forth in SEQ ID NO: 1. Then, Patent Literatures 2 and 3 describe that the productivity of medium-chain fatty acids having 8 or 10 carbon atoms is improved by introducing a gene encoding such a TE variant into a host such as *Escherichia coli* and cyanobacteria.

In recent years, attention has been attracted on a method of producing biochemicals including fatty acids by culturing cyanobacteria or *Escherichia coli* using a renewable energy source such as sunlight and biomass. For example, as biofuels produced using cyanobacteria, ethanol (Non-Patent Literature 2), isobutanol (Non-Patent Literature 3), fatty acids (Non-Patent Literature 4) and the like have been reported.

CITATION LIST

Patent Literatures

Patent literature 1: WO 92/20236 A1
Patent literature 2: U.S. Pat. No. 5,955,329 A
Patent literature 3: US 2011/0020883 A

Non-Patent Literatures

Non-patent literature 1: Science, 1992, vol. 257(5066), p. 72-74
Non-patent literature 2: Appl. Environ. Microbiol., 1999, 65:523-528
Non-patent literature 3: Nat. Biotechnol., 2009, vol. 27, p. 1177-1180
Non-patent literature 4: Proc. Natl. Acad. Sci. USA., 2011, vol. 108(17), p. 6899-6904

SUMMARY OF INVENTION

The present invention relates to a method of producing lipids, containing the steps of:

culturing a transformant into which a gene encoding at least one protein selected from the group consisting of the following proteins (A) to (C) is introduced; and producing fatty acids or lipids containing the same as components:

(A) a protein consisting of an amino acid sequence having at least one amino acid substitution selected from the group consisting of the following (A-1) to (A-11) in the amino acid sequence set forth in SEQ ID NO: 1, and having acyl-ACP thioesterase activity;

(B) a protein consisting of an amino acid sequence having at least one amino acid substitution selected from the group consisting of the following (B-1) to (B-11) in an amino acid sequence having 85% or more identity with the amino acid sequence set forth in SEQ ID NO: 1, and having acyl-ACP thioesterase activity; and (C) a protein containing the amino acid sequence of the protein (A) or (B), and having acyl-ACP thioesterase activity:

(A-1) substitution of isoleucine for leucine at position 257 of the amino acid sequence set forth in SEQ ID NO: 1;
(A-2) substitution of arginine for threonine at position 251 of the amino acid sequence set forth in SEQ ID NO: 1;
(A-3) substitution of lysine for threonine at position 251 of the amino acid sequence set forth in SEQ ID NO: 1;
(A-4) substitution of histidine for threonine at position 251 of the amino acid sequence set forth in SEQ ID NO: 1;
(A-5) substitution of isoleucine for tryptophan at position 254 of the amino acid sequence set forth in SEQ ID NO: 1;

(A-6) substitution of tyrosine for tryptophan at position 254 of the amino acid sequence set forth in SEQ ID NO: 1;
(A-7) substitution of methionine for leucine at position 257 of the amino acid sequence set forth in SEQ ID NO: 1;
(A-8) substitution of valine for leucine at position 257 of the amino acid sequence set forth in SEQ ID NO: 1;
(A-9) substitution of phenylalanine for leucine at position 257 of the amino acid sequence set forth in SEQ ID NO: 1;
(A-10) substitution of cysteine for valine at position 266 of the amino acid sequence set forth in SEQ ID NO: 1;
(A-11) substitution of tyrosine for tryptophan at position 271 of the amino acid sequence set forth in SEQ ID NO: 1;
(B-1) substitution of isoleucine for an amino acid at a position corresponding to position 257 of the amino acid sequence set forth in SEQ ID NO: 1;
(B-2) substitution of arginine for an amino acid at a position corresponding to position 251 of the amino acid sequence set forth in SEQ ID NO: 1;
(B-3) substitution of lysine for an amino acid at a position corresponding to position 251 of the amino acid sequence set forth in SEQ ID NO: 1;
(B-4) substitution of histidine for an amino acid at a position corresponding to position 251 of the amino acid sequence set forth in SEQ ID NO: 1;
(B-5) substitution of isoleucine for an amino acid at a position corresponding to position 254 of the amino acid sequence set forth in SEQ ID NO: 1;
(B-6) substitution of tyrosine for an amino acid at a position corresponding to position 254 of the amino acid sequence set forth in SEQ ID NO: 1;
(B-7) substitution of methionine for an amino acid at a position corresponding to position 257 of the amino acid sequence set forth in SEQ ID NO: 1;
(B-8) substitution of valine for an amino acid at a position corresponding to position 257 of the amino acid sequence set forth in SEQ ID NO: 1;
(B-9) substitution of phenylalanine for an amino acid at a position corresponding to position 257 of the amino acid sequence set forth in SEQ ID NO: 1;
(B-10) substitution of cysteine for an amino acid at a position corresponding to position 266 of the amino acid sequence set forth in SEQ ID NO: 1;
(B-11) substitution of tyrosine for an amino acid at a position corresponding to position 271 of the amino acid sequence set forth in SEQ ID NO: 1.

Further, the present invention relates to a method of producing lipids, containing the steps of: culturing a transformant into which a gene encoding at least one protein selected from the group consisting of the proteins (A) to (C) is introduced; and improving the productivity of medium-chain fatty acids or lipids containing the same as components, produced in a cell of the transformant.

Further, the present invention relates to a method of modifying fatty acid composition, containing the steps of: culturing a transformant into which a gene encoding at least one protein selected from the group consisting of the proteins (A) to (C) is introduced; and increasing the proportion of medium-chain fatty acids in whole fatty acids produced in a cell of the transformant.

Further, the present invention relates to the proteins (A) to (C).

Further, the present invention relates to a gene encoding any one of the proteins (A) to (C).

Furthermore, the present invention relates to a transformant containing a gene encoding any one of the proteins (A) to (C).

Other and further features and advantages of the invention will appear more fully from the following description.

MODE FOR CARRYING OUT THE INVENTION

The present invention relates to providing a method of producing lipids, which improves productivity of medium-chain fatty acids or lipids containing the same as components.

Further, the present invention relates to providing a transformant in which the productivity of medium-chain fatty acids or lipids containing the same as components is improved, and which can be preferably used for the above-described method.

Further, the present invention relates to providing a novel TE variant and a gene encoding the same, which are preferably used for the above-described method and transformant.

As reported in Patent Literatures 2, 3 and the like, attempts have been made to improve fatty acid production also with regard to production of medium-chain fatty acids by using a transformant of *Escherichia coli*, cyanobacteria or the like into which a gene encoding a TE derived from plants belonging to the genus *Cuphea* is introduced.

With an eye to improving productivity of medium-chain fatty acids, the present inventors conducted a study on such technology with focus on site of amino-acid substitution in a wild-type TE derived from plants belonging to the genus *Cuphea*. The results of this study led the present inventors to conclude that use of a TE variant in which an amino acid substitution was occurred at a site different from those disclosed in Patent Literatures 2 and 3 and other reports is effective for enhanced production of medium-chain fatty acids.

The present invention was completed based on these findings.

According to the method of producing the lipids of the present invention, the productivity of medium-chain fatty acids or lipids containing the same as components can be improved.

Moreover, the transformant of the present invention is excellent in the productivity of medium-chain fatty acids or lipids containing the same as components.

Further, the acyl-ACP thioesterase variant and the gene encoding the same of the present invention can be preferably used for production of medium-chain fatty acids or lipids containing the same as components.

The term "lipid(s)" in the present specification, covers a simple lipid such as a neutral lipid (monoacylglycerol (MAG), diacylglycerol (DAG), triacylglycerol (TAG), or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, the fatty acid group or the acyl group in molecules of a simple lipid and a complex lipid is expressed as "fatty acid residue". Then, unless otherwise specified, a term "fatty acid" is used as a generic term for "free fatty acid" and "fatty acid residue".

Moreover, a term "fatty acids or lipids containing the same as components" in the present specification is generically used including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above regarding as fatty acids. The weight (production amount) of the fatty acids or the fatty acid composition can be measured according to the method used in Examples.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The amino acid sequence set forth in SEQ ID NO: 1 is a part of an amino acid sequence of a wild-type TE derived from *Cuphea palustris* which consists of the amino acid sequence set forth in SEQ ID NO: 48. In the amino acid sequence set forth in SEQ ID NO: 1, region of putative signal sequence (amino acid sequence at positions 2 to 57 of SEQ ID NO: 48) is deleted from the full length of amino acid sequence of the wild-type TE. That is, in the amino acid sequence set forth in SEQ ID NO: 1, amino acids at positions 1 to 57 are removed from the amino acid sequence set forth in SEQ ID NO: 48, and a protein synthesis initiation amino acid (methionine) is added to N-terminal side of amino acid at position 58. A TE derived from plants belonging to the genus *Cuphea* has high specificity to the medium-chain acyl-ACP having 8 or 10 carbon atoms, and thereby the TE is suitably used for improvement of productivity of medium-chain fatty acids having 8 or 10 carbon atoms in a transformant.

In the present invention, any of amino acid substitutions of the (A-1) to (A-11) and (B-1) to (B-11) is provided with the wild-type TE derived from *Cuphea palustris* having substrate specificity to medium-chain fatty acid having 8 or 10 carbon atoms. Thus amino acid substituted TE variant of the present invention has improved substrate specificity to medium-chain acyl-ACP, in comparison to the wild-type TE. Moreover, a transformant into which a gene encoding the TE variant of the present invention is excellent in the productivity of medium-chain fatty acids.

In addition, in the present specification, the wild-type TE derived from *Cuphea palustris* together with the TE variant, wherein amino acid mutation is carried out in wild-type TE, are also referred to as "CpTE".

Patent Literatures 2 and 3 disclose that, when amino acid substitution is performed in regions at positions 172 to 221 of the amino acid sequence of CpTE (amino acid sequence set forth in SEQ ID NO: 1), substrate specificity of the TE variant to the medium-chain acyl-ACP is improved.

On the other hand, in the present invention, as specified in the above-described (A-1) to (A-11) and (B-1) to (B-11), amino-acid substitution in a site different from the sites disclosed in Patent Literatures 2 and 3 is carried out.

In the transformant of the present invention, a gene encoding at least one protein (acyl-ACP thioesterase variant) selected from the group consisting of the proteins (A) to (C) is introduced, and expression thereof is enhanced. Productivity of medium-chain fatty acids or lipids containing the same as components produced in a cell of the transformant is improved by culturing the transformant of the present invention.

The acyl-ACP thioesterase variant (hereinafter, also referred to as "TE variant") is a protein having an amino acid sequence wherein a part of amino acid sequence set forth in SEQ ID NO: 1 is modified, and having acyl-ACP thioesterase activity (hereinafter, also referred to as "TE activity").

Note that, in the present specification, the term "medium-chain" means that the number of carbon atoms of the acyl group is 8 or more and 10 or less, and preferably 8 or 10. The productivity of fatty acids and lipids of the transformant can be measured by the method used in Examples described below.

The amino acid sequence set forth in SEQ ID NO: 1 is an amino acid sequence whose amino acid sequence at positions 2 to 57 of the amino acid sequence set forth in SEQ ID NO: 48 is deleted from the N-terminal end thereof, and corresponds to amino acid sequence at positions 1, 58 to 411 of the amino acid sequence set forth in SEQ ID NO: 48. SEQ ID NO: 48 is an amino acid sequence of a wild-type TE derived from *Cuphea palustris*. It is known that the region of the 58th to 411st positions in the amino acid sequence set forth in SEQ ID NO: 48 is an important and sufficient region for exhibiting the TE activity. That is, the protein consisting of the amino acid sequence set forth in SEQ ID NO: 1 has the TE activity and acts as TE, because the protein has the sufficient region for the TE activity.

TE is an enzyme involved in the biosynthesis pathway of fatty acids and derivatives thereof (such as triacylglycerol (triglyceride)). This enzyme hydrolyzes a thioester bond of an acyl-ACP (a composite composed of an acyl group as a fatty acid residue and an acyl carrier protein), which is an intermediate in the process of fatty acid biosynthesis, to form free fatty acids in a plastid such as a chloroplast of plants and algae or in a cytoplasm of bacteria, fungi and animals. The function of the TE terminates the fatty acid synthesis on the ACP, and then the thus-hydrolyzed fatty acid is supplied to the synthesis of triacylglycerol or the like. Several TEs having different reaction specificities depending on the number of carbon atoms and the number of unsaturated bonds of the acyl group (fatty acid residue) constituting the acyl-ACP substrate are identified, and TE is considered to be an important factor in determining the fatty acid composition of an organism.

In the present specification, the term "TE activity" means an activity of hydrolyzing the thioester bond of the acyl-ACP.

The amino acid sequence of the protein (A) is basically the amino acid sequence set forth in SEQ ID NO: 1, and amino acids at specific positions in the amino acid sequence are replaced by those shown by any of the (A-1) to (A-11).

Specificity to the medium-chain acyl-ACP is improved in the TE variant specified as the protein (A). That is, in comparison with the wild type TE, the TE variant of the protein (A) selectively utilizes medium-chain acyl-ACP as a substrate and has improved activity of hydrolyzing this substrate.

From viewpoints of improving specificity to the medium-chain acyl-ACP, and improving productivity of medium-chain fatty acids or lipids containing the same as components, the amino acid sequence of the protein (A) preferably has amino acid substitution of the (A-1).

In the present specification, TE variants having an amino acid substitution may be abbreviated as described below:
CpTE(L257I) or L257I: TE variant in which isoleucine (I) is substituted for leucine (L) at position 257 of the amino acid sequence set forth in SEQ ID NO: 1;
CpTE(T251R) or T251R: TE variant in which arginine (R) is substituted for threonine (T) at position 251 of the amino acid sequence set forth in SEQ ID NO: 1;
CpTE(T251K) or T251K: TE variant in which lysine (K) is substituted for threonine (T) at position 251 of the amino acid sequence set forth in SEQ ID NO: 1;
CpTE(T251H) or T251H: TE variant in which histidine (H) is substituted for threonine (T) at position 251 of the amino acid sequence set forth in SEQ ID NO: 1;
CpTE(W254I) or W254I: TE variant in which isoleucine (I) is substituted for tryptophan (W) at position 254 of the amino acid sequence set forth in SEQ ID NO: 1;
CpTE(W254Y) or W254Y: TE variant in which tyrosine (Y) is substituted for tryptophan (W) at position 254 of the amino acid sequence set forth in SEQ ID NO: 1;
CpTE(L257M) or L257M: TE variant in which methionine (M) is substituted for leucine (L) at position 257 of the amino acid sequence set forth in SEQ ID NO: 1;
CpTE(L257V) or L257V: TE variant in which valine (V) is substituted for leucine (L) at position 257 of the amino acid sequence set forth in SEQ ID NO: 1;
CpTE(L257F) or L257F: TE variant in which phenylalanine (F) is substituted for leucine (L) at position 257 of the amino acid sequence set forth in SEQ ID NO: 1;
CpTE(V266C) or V266C: TE variant in which cysteine (C) is substituted for valine (V) at position 266 of the amino acid sequence set forth in SEQ ID NO: 1;
CpTE(W271Y) or W271Y: TE variant in which tyrosine (Y) is substituted for tryptophan (W) at position 271 of the amino acid sequence set forth in SEQ ID NO: 1.

The protein (A) preferably has at least one amino acid substitution selected from the group consisting of the following (D-1) to (D-8), in addition to at least one amino acid substitution selected from the group consisting of the (A-1) to (A-11). In a case having these amino acid substitutions, the specificity to the medium-chain acyl-ACP and productivity of medium-chain fatty acids or lipids containing the same as components are further improved.

In the present invention, the protein (A) preferably has the amino acid substitution of (A-1) and at least one amino acid substitution selected from the group consisting of the following (D-1) to (D-8), and more preferably has the amino acid substitution of (A-1) and one amino acid substitution selected from the group consisting of the following (D-1) to (D-8).
(D-1) substitution of isoleucine for valine at position 106 of the amino acid sequence set forth in SEQ ID NO: 1;
(D-2) substitution of lysine for asparagine at position 108 of the amino acid sequence set forth in SEQ ID NO: 1;
(D-3) substitution of arginine for asparagine at position 108 of the amino acid sequence set forth in SEQ ID NO: 1;
(D-4) substitution of isoleucine for valine at position 110 of the amino acid sequence set forth in SEQ ID NO: 1;
(D-5) substitution of methionine for valine at position 110 of the amino acid sequence set forth in SEQ ID NO: 1;
(D-6) substitution of leucine for valine at position 110 of the amino acid sequence set forth in SEQ ID NO: 1;
(D-7) substitution of phenylalanine for valine at position 110 of the amino acid sequence set forth in SEQ ID NO: 1;
(D-8) substitution of isoleucine for cysteine at position 118 of the amino acid sequence set forth in SEQ ID NO: 1.

In the present specification, amino acid substitutions of the (D-1) to (D-8) may be abbreviated as described below:
V106I: substitution of isoleucine (I) for valine (V) at position 106 of the amino acid sequence set forth in SEQ ID NO: 1;
N108K: substitution of lysine (K) for asparagine (N) at position 108 of the amino acid sequence set forth in SEQ ID NO: 1;
N108R: substitution of arginine (R) for asparagine (N) at position 108 of the amino acid sequence set forth in SEQ ID NO: 1;
V110I: substitution of isoleucine (I) for valine (V) at position 110 of the amino acid sequence set forth in SEQ ID NO: 1;
V110M: substitution of methionine (M) for valine (V) at position 110 of the amino acid sequence set forth in SEQ ID NO: 1;
V110L: substitution of leucine (L) for valine (V) at position 110 of the amino acid sequence set forth in SEQ ID NO: 1;
V110F: substitution of phenylalanine (F) for valine (V) at position 110 of the amino acid sequence set forth in SEQ ID NO: 1;
C118I: substitution of isoleucine (I) for cysteine (C) at position 118 of the amino acid sequence set forth in SEQ ID NO: 1.

In the present invention, the protein (A) preferably has amino acid substitutions selected from the group consisting of the following (A-1_D-1) to (A-1_D-8):
(A-1_D-1) substitutions of isoleucine for leucine at position 257, and isoleucine for valine at position 106 of the amino acid sequence set forth in SEQ ID NO: 1;
(A-1_D-2) substitutions of isoleucine for leucine at position 257, and lysine for asparagine at position 108 of the amino acid sequence set forth in SEQ ID NO: 1;
(A-1_D-3) substitutions of isoleucine for leucine at position 257, and arginine for asparagine at position 108 of the amino acid sequence set forth in SEQ ID NO: 1;
(A-1_D-4) substitutions of isoleucine for leucine at position 257, and isoleucine for valine at position 110 of the amino acid sequence set forth in SEQ ID NO: 1;
(A-1_D-5) substitutions of isoleucine for leucine at position 257, and methionine for valine at position 110 of the amino acid sequence set forth in SEQ ID NO: 1;
(A-1_D-6) substitutions of isoleucine for leucine at position 257, and leucine for valine at position 110 of the amino acid sequence set forth in SEQ ID NO: 1;
(A-1_D-7) substitutions of isoleucine for leucine at position 257, and phenylalanine for valine at position 110 of the amino acid sequence set forth in SEQ ID NO: 1; and
(A-1_D-8) substitutions of isoleucine for leucine at position 257, and isoleucine for cysteine at position 118 of the amino acid sequence set forth in SEQ ID NO: 1.

The protein (B) basically consists of an amino acid sequence having 85% or more identity with the amino acid sequence set forth in SEQ ID NO: 1, and having TE activity. In the protein (B), as similar to the protein (A), specificity to a medium-chain acyl-ACP is improved.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the TE activity is kept and a part of the amino acid sequence is subjected to mutation.

In the protein (B), the identity with the amino acid sequence set forth in SEQ ID NO: 1 is preferably 85% or more, more preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of TE activity.

Further, specific examples of the protein (B) include a protein in which 1 or several (for example 1 or more and 53 or less, preferably 1 or more and 35 or less, more preferably 1 or more and 28 or less, further preferably 1 or more and 24 or less, furthermore preferably 1 or more and 21 or less, furthermore preferably 1 or more and 17 or less, furthermore preferably 1 or more and 14 or less, furthermore preferably 1 or more and 10 or less, furthermore preferably 1 or more and 7 or less, and furthermore preferably 1 or more and 3 or less) amino acids are deleted, substituted, inserted or added to the amino acid sequence set forth in SEQ ID NO: 1, and having TE activity. Further, these amino acid mutations are different with the amino acid substitutions of (B-1) to (B-11).

Furthermore, the amino acid sequence of the protein (B) contains an amino acid substitution corresponding to the amino acid substitution in the protein (A), in an amino acid sequence having 85% or more identity with the amino acid sequence set forth in SEQ ID NO: 1. Accordingly, the amino acid sequence of the protein (B) contains at least one amino acid substitution selected from the group consisting of the (B-1) to (B-11).

Herein, an amino acid at a position corresponding to position 251 of the amino acid sequence set forth in SEQ ID NO: 1 is preferably or generally threonine. An amino acid at a position corresponding to position 254 of the amino acid sequence set forth in SEQ ID NO: 1 is preferably or generally tryptophan. An amino acid at a position corresponding to position 257 of the amino acid sequence set forth in SEQ ID NO: 1 is preferably or generally leucine. An amino acid at a position corresponding to position 266 of the amino acid sequence set forth in SEQ ID NO: 1 is preferably or generally valine. An amino acid at a position corresponding to position 271 of the amino acid sequence set forth in SEQ ID NO: 1 is preferably or generally tryptophan.

As similar to that of the protein (A) described above, the amino acid sequence of the protein (B) preferably has the amino acid substitution of (B-1).

The protein (B) preferably has at least one amino acid substitution selected from the group consisting of the following (E-1) to (E-8), in addition to at least one amino acid substitution selected from the group consisting of the (B-1) to (B-11). In a case having these amino acid substitutions, the specificity of the medium-chain acyl-ACP and productivity of medium-chain fatty acids or lipids containing the same as components are further improved.

In the present invention, the protein (B) preferably has the amino acid substitution of (B-1) and at least one amino acid substitution selected from the group consisting of the following (E-1) to (E-8), and more preferably has the amino acid substitution of (B-1) and one amino acid substitution selected from the group consisting of the following (E-1) to (E-8).

(E-1) substitution of isoleucine for an amino acid at a position corresponding to position 106 of the amino acid sequence set forth in SEQ ID NO: 1;
(E-2) substitution of lysine for an amino acid at a position corresponding to position 108 of the amino acid sequence set forth in SEQ ID NO: 1;
(E-3) substitution of arginine for an amino acid at a position corresponding to position 108 of the amino acid sequence set forth in SEQ ID NO: 1;
(E-4) substitution of isoleucine for an amino acid at a position corresponding to position 110 of the amino acid sequence set forth in SEQ ID NO: 1;
(E-5) substitution of methionine for an amino acid at a position corresponding to position 110 of the amino acid sequence set forth in SEQ ID NO: 1;
(E-6) substitution of leucine for an amino acid at a position corresponding to position 110 of the amino acid sequence set forth in SEQ ID NO: 1;
(E-7) substitution of phenylalanine for an amino acid at a position corresponding to position 110 of the amino acid sequence set forth in SEQ ID NO: 1; and
(E-8) substitution of isoleucine for an amino acid at a position corresponding to position 118 of the amino acid sequence set forth in SEQ ID NO: 1.

Herein, an amino acid at a position corresponding to position 106 of the amino acid sequence set forth in SEQ ID NO: 1 is preferably or generally valine. An amino acid at a position corresponding to position 108 of the amino acid sequence set forth in SEQ ID NO: 1 is preferably or generally asparagine. An amino acid at a position corresponding to position 110 of the amino acid sequence set forth in SEQ ID NO: 1 is preferably or generally valine. An amino acid at a position corresponding to position 118 of the amino acid sequence set forth in SEQ ID NO: 1 is preferably or generally cysteine.

In the present invention, the protein (B) more preferably has amino acid substitutions selected from the group consisting of the following (B-1_E-1) to (B-1_E-8):
(B-1_E-1) substitutions of isoleucine for an amino acid at a position corresponding to position 257 (preferably or generally, leucine), and isoleucine for an amino acid at a position corresponding to position 106 (preferably or generally, valine) of the amino acid sequence set forth in SEQ ID NO: 1;
(B-1_E-2) substitutions of isoleucine for an amino acid at a position corresponding to position 257 (preferably or generally, leucine), and lysine for an amino acid at a position corresponding to position 108 (preferably or generally, asparagine) of the amino acid sequence set forth in SEQ ID NO: 1;
(B-1_E-3) substitutions of isoleucine for an amino acid at a position corresponding to position 257 (preferably or generally, leucine), and arginine for an amino acid at a position corresponding to position 108 (preferably or generally, asparagine) of the amino acid sequence set forth in SEQ ID NO: 1;
(B-1_E-4) substitutions of isoleucine for an amino acid at a position corresponding to position 257 (preferably or generally, leucine), and isoleucine for an amino acid at a position corresponding to position 110 (preferably or generally, valine) of the amino acid sequence set forth in SEQ ID NO: 1;

(B-1_E-5) substitutions of isoleucine for an amino acid at a position corresponding to position 257 (preferably or generally, leucine), and methionine for an amino acid at a position corresponding to position 110 (preferably or generally, valine) of the amino acid sequence set forth in SEQ ID NO: 1;

(B-1_E-6) substitutions of isoleucine for an amino acid at a position corresponding to position 257 (preferably or generally, leucine), and leucine for an amino acid at a position corresponding to position 110 (preferably or generally, valine) of the amino acid sequence set forth in SEQ ID NO: 1;

(B-1_E-7) substitutions of isoleucine for an amino acid at a position corresponding to position 257 (preferably or generally, leucine), and phenylalanine for an amino acid at a position corresponding to position 110 (preferably or generally, valine) of the amino acid sequence set forth in SEQ ID NO: 1; and (B-1_E-8) substitutions of isoleucine for an amino acid at a position corresponding to position 257 (preferably or generally, leucine), and isoleucine for an amino acid at a position corresponding to position 118 (preferably or generally, cysteine) of the amino acid sequence set forth in SEQ ID NO: 1.

The "position corresponding thereto" or "region corresponding thereto" in the amino acid sequence or the nucleotide sequence can be determined by comparing an objective amino acid sequence with a reference sequence to align (provide alignment to) the sequence so as to give the maximum homology for a conserved amino acid residue existing in each amino acid sequence. The alignment can be executed by using a publicly known algorithm, and the procedures are publicly known to a person skilled in the art. The alignment can be manually performed, for example, based on the Lipman-Pearson method mentioned above; or alternatively, can be performed by using the Clustal W multiple alignment program (Nucleic Acids Res., 1994, vol. 22, p. 4673-4680) by default. The Clustal W is available from websites: for example, European Bioinformatics Institute: EBI, (www.ebi.ac.uk/index.html) and DNA Data Bank of Japan (DDBJ, [www.ddbj.nig.ac.jp/Welcome-j.html]) managed by the National Institute of Genetics.

The protein (C) contains the amino acid sequence of the protein (A) or (B) as a part of the amino acid sequence of the protein (C), and exhibits TE activity. Further, an amino acid at N-terminal end of the protein (C) is preferably methionine or leucine encoded by a start codon.

In the amino acid sequence constituting the above-described protein (C), a sequence other than the amino acid sequence of the above-described protein (A) or (B) can be appropriately selected within the range in which advantageous effects of the invention are not adversely affected. The examples thereof the arbitrary amino acid sequence of 1st to 57th amino acids of the amino acid sequence set forth in SEQ ID NO: 48, an amino acid sequence in which 1 or several (preferably 1 or more and 20 or less, more preferably 1 or more and 15 or less, further preferably 1 or more and 10 or less, furthermore preferably 1 or more and 5 or less, and furthermore preferably 1 or more and 3 or less) mutations are introduced into the amino acid sequence, and the like. The examples of the mutation include deletion, substitution, insertion and addition of amino acids. These sequences are preferably added to the N-terminal side of the amino acid sequence of the protein (A) or (B).

Alternatively, the above-described protein (C) may be a protein consisting of the amino acid sequence in which a portion on the N-terminal side is deleted in an arbitrary position of the $2^{nd}$ to $57^{th}$ amino acids of the amino acid sequence set forth in SEQ ID NO: 48 in the amino acid sequence set forth in SEQ ID NO: 48. Moreover, the protein (C) also preferably includes a protein consisting of an amino acid sequence formed such that a signal peptide involved in transport or secretion of the protein is added to the amino acid sequence of the protein (A) or (B).

The TE activity of the protein can be confirmed by, for example, introducing a DNA produced by linking a gene encoding the protein to the downstream of a promoter which functions in a host cell such as *Escherichia coli*, into a host cell which lacks a fatty acid degradation system, culturing the thus-obtained cell under the conditions suitable for the expression of the introduced gene, and analyzing any change caused thereby in the fatty acid composition of the host cell or the cultured liquid by using a gas chromatographic analysis or the like. In this case, improving specificity to the medium-chain acyl-ACP in the TE variant can be confirmed by comparing a proportion of medium-chain fatty acids in the total amount of fatty acids with a proportion of a system in which the wild type TE is expressed.

Alternatively, the TE activity can be measured by introducing a DNA produced by linking a gene encoding the protein to the downstream of a promoter which functions in a host cell such as *Escherichia coli*, into a host cell, culturing the thus-obtained cell under the conditions suitable for the expression of the introduced gene, and subjecting a disruption liquid of the cell to a reaction which uses acyl-ACPs, as substrates, prepared according to the method of Yuan et al. (Proc. Natl. Acad. Sci. USA., 1995, vol. 92(23), p. 10639-10643).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) to (C) can be obtained by chemical techniques, genetic engineering techniques or the like that are ordinarily carried out. For example, a natural product-derived protein can be obtained through isolation, purification and the like from *Cuphea palustris*. In addition, the proteins (A) to (C) can be obtained by artificial chemical synthesis based on the amino acid sequence set forth in SEQ ID NO: 1. Alternatively, as recombinant proteins, proteins (A) to (C) may also be produced by gene recombination technologies. In the case of producing a recombinant protein, the TE gene described below can be used.

Note that the plant such as *Cuphea palustris* can be obtained from culture collection such as private or public research institutes or the like.

Examples of genes encoding at least one protein selected form the group consisting of the proteins (A) to (C) (hereinafter, also referred to as "TE variant gene" or "CpTE variant gene") include a gene consisting of any one of the following DNAs (a) to (c). The DNA consisting of the nucleotide sequence set forth in SEQ ID NO: 2 encodes the protein consisting of the amino acid sequence set forth in SEQ ID NO: 1 (wild-type TE derived from *Cuphea palustris*). Further, the nucleotide sequence encoding the signal sequence (amino acid sequence of the 1st to 57th amino acids of the amino acid sequence set forth in SEQ ID NO: 48) corresponds to the nucleotide sequence of the 1st to 171st nucleotides of the nucleotide sequence set forth in SEQ ID NO: 49.

(a) a DNA consisting of a nucleotide sequence having at least one nucleotide substitution selected from the group consisting of the following (a-1) to (a-11) in the nucleotide sequence set forth in SEQ ID NO: 2, and encoding a protein having TE activity;
(b) a DNA consisting of a nucleotide sequence having at least one nucleotide substitution selected from the group consisting of the following (b-1) to (b-11) in a nucleotide sequence having 70% or more identity with the nucleotide sequence set forth in SEQ ID NO: 2, and encoding a protein having TE activity; and
(c) a DNA containing the nucleotide sequence of the DNA (a) or (b) (preferably, a nucleotide sequence of the DNA (a) or (b) except for the start codon), and encoding a protein having TE activity:
(a-1) substitution of nucleotides encoding isoleucine for nucleotides at positions 769 to 771 of the nucleotide sequence set forth in SEQ ID NO: 2; (a-2) substitution of nucleotides encoding arginine for nucleotides at positions 751 to 753 of the nucleotide sequence set forth in SEQ ID NO: 2;
(a-3) substitution of nucleotides encoding lysine for nucleotides at positions 751 to 753 of the nucleotide sequence set forth in SEQ ID NO: 2
(a-4) substitution of nucleotides encoding histidine for nucleotides at positions 751 to 753 of the nucleotide sequence set forth in SEQ ID NO: 2;
(a-5) substitution of nucleotides encoding isoleucine for nucleotides at positions 760 to 762 of the nucleotide sequence set forth in SEQ ID NO: 2;
(a-6) substitution of nucleotides encoding tyrosine for nucleotides at positions 760 to 762 of the nucleotide sequence set forth in SEQ ID NO: 2;
(a-7) substitution of nucleotides encoding methionine for nucleotides at positions 769 to 771 of the nucleotide sequence set forth in SEQ ID NO: 2;
(a-8) substitution of nucleotides encoding valine for nucleotides at positions 769 to 771 of the nucleotide sequence set forth in SEQ ID NO: 2;
(a-9) substitution of nucleotides encoding phenylalanine for nucleotides at positions 769 to 771 of the nucleotide sequence set forth in SEQ ID NO: 2;
(a-10) substitution of nucleotides encoding cysteine for nucleotides at positions 796 to 798 of the nucleotide sequence set forth in SEQ ID NO: 2;
(a-11) substitution of nucleotides encoding tyrosine for nucleotides at positions 811 to 813 of the nucleotide sequence set forth in SEQ ID NO: 2;
(b-1) substitution of nucleotides encoding isoleucine for nucleotides at positions corresponding to positions 769 to 771 of the nucleotide sequence set forth in SEQ ID NO: 2;
(b-2) substitution of nucleotides encoding arginine for nucleotides at positions corresponding to positions 751 to 753 of the nucleotide sequence set forth in SEQ ID NO: 2;
(b-3) substitution of nucleotides encoding lysine for nucleotides at positions corresponding to positions 751 to 753 of the nucleotide sequence set forth in SEQ ID NO: 2;
(b-4) substitution of nucleotides encoding histidine for nucleotides at positions corresponding to positions 751 to 753 of the nucleotide sequence set forth in SEQ ID NO: 2;
(b-5) substitution of nucleotides encoding isoleucine for nucleotides at positions corresponding to positions 760 to 762 of the nucleotide sequence set forth in SEQ ID NO: 2;
(b-6) substitution of nucleotides encoding tyrosine for nucleotides at positions corresponding to positions 760 to 762 of the nucleotide sequence set forth in SEQ ID NO: 2;
(b-7) substitution of nucleotides encoding methionine for nucleotides at positions corresponding to positions 769 to 771 of the nucleotide sequence set forth in SEQ ID NO: 2;
(b-8) substitution of nucleotides encoding valine for nucleotides at positions corresponding to positions 769 to 771 of the nucleotide sequence set forth in SEQ ID NO: 2;
(b-9) substitution of nucleotides encoding phenylalanine for nucleotides at positions corresponding to positions 769 to 771 of the nucleotide sequence set forth in SEQ ID NO: 2;
(b-10) substitution of nucleotides encoding cysteine for nucleotides at positions corresponding to positions 796 to 798 of the nucleotide sequence set forth in SEQ ID NO: 2; and
(b-11) substitution of nucleotides encoding tyrosine for nucleotides at positions corresponding to positions 811 to 813 of the nucleotide sequence set forth in SEQ ID NO: 2.

The nucleotide sequence of DNA (a) has nucleotide substitutions corresponding to the amino acid substitutions in the amino acid sequence of the protein (A). Specifically, the nucleotide substitutions of (a-1), (a-2), (a-3), (a-4), (a-5), (a-6), (a-7), (a-8), (a-9), (a-10), and (a-11) respectively correspond to the amino acid substitutions of (A-1), (A-2), (A-3), (A-4), (A-5), (A-6), (A-7), (A-8), (A-9), (A-10), and (A-11).

Similarly, the nucleotide sequence of DNA (b) has the nucleotide substitutions corresponding to the amino acid substitutions in the amino acid sequence of the protein (B). Specifically, the nucleotide substitutions of (b-1), (b-2), (b-3), (b-4), (b-5), (b-6), (b-7), (b-8), (b-9), (b-10), and (b-11) respectively correspond to the amino acid substitutions of (B-1), (B-2), (B-3), (B-4), (B-5), (B-6), (B-7), (B-8), (B-9), (B-10), and (B-11).

The DNA (a) preferably has at least one nucleotide substitution selected from the group consisting of the following (d-1) to (d-8), in addition to at least one nucleotide substitution selected from the group consisting of the (a-1) to (a-11). In the present invention, the DNA(a) more preferably has the nucleotide substitution of (a-1) and at least one nucleotide substitution selected from the group consisting of the following (d-1) to (d-8).

(d-1) substitution of nucleotides encoding isoleucine for nucleotides at positions 316 to 318 of the nucleotide sequence set forth in SEQ ID NO: 2;
(d-2) substitution of nucleotides encoding lysine for nucleotides at positions 322 to 324 of the nucleotide sequence set forth in SEQ ID NO: 2;
(d-3) substitution of nucleotides encoding arginine for nucleotides at positions 322 to 324 of the nucleotide sequence set forth in SEQ ID NO: 2;
(d-4) substitution of nucleotides encoding isoleucine for nucleotides at positions 328 to 330 of the nucleotide sequence set forth in SEQ ID NO: 2;
(d-5) substitution of nucleotides encoding methionine for nucleotides at positions 328 to 330 of the nucleotide sequence set forth in SEQ ID NO: 2;

(d-6) substitution of nucleotides encoding leucine for nucleotides at positions 328 to 330 of the nucleotide sequence set forth in SEQ ID NO: 2;
(d-7) substitution of nucleotides encoding phenylalanine for nucleotides at positions 328 to 330 of the nucleotide sequence set forth in SEQ ID NO: 2; and
(d-8) substitution of nucleotides encoding isoleucine for nucleotides at positions 352 to 354 of the nucleotide sequence set forth in SEQ ID NO: 2.

In the present invention, the DNA (a) preferably has the nucleotide substitution selected from the group consisting of the following (a-1_d-1) to (a-1_d-8):
(a-1_d-1) substitutions of nucleotides encoding isoleucine for nucleotides at positions 769 to 771, and nucleotides encoding isoleucine for nucleotides at positions 316 to 318 of the nucleotide sequence set forth in SEQ ID NO: 2;
(a-1_d-2) substitutions of nucleotides encoding isoleucine for nucleotides at positions 769 to 771, and nucleotides encoding lysine for nucleotides at positions 322 to 324 of the nucleotide sequence set forth in SEQ ID NO: 2;
(a-1_d-3) substitutions of nucleotides encoding isoleucine for nucleotides at positions 769 to 771, and nucleotides encoding arginine for nucleotides at positions 322 to 324 of the nucleotide sequence set forth in SEQ ID NO: 2;
(a-1_d-4) substitutions of nucleotides encoding isoleucine for nucleotides at positions 769 to 771, and nucleotides encoding isoleucine for nucleotides at positions 328 to 330 of the nucleotide sequence set forth in SEQ ID NO: 2;
(a-1_d-5) substitutions of nucleotides encoding isoleucine for nucleotides at positions 769 to 771, and nucleotides encoding methionine for nucleotides at positions 328 to 330 of the nucleotide sequence set forth in SEQ ID NO: 2;
(a-1_d-6) substitutions of nucleotides encoding isoleucine for nucleotides at positions 769 to 771, and nucleotides encoding leucine for nucleotides at positions 328 to 330 of the nucleotide sequence set forth in SEQ ID NO: 2;
(a-1_d-7) substitutions of nucleotides encoding isoleucine for nucleotides at positions 769 to 771, and nucleotides encoding phenylalanine for nucleotides at positions 328 to 330 of the nucleotide sequence set forth in SEQ ID NO: 2; and
(a-1_d-8) substitutions of nucleotides encoding isoleucine for nucleotides at positions 769 to 771, and nucleotides encoding isoleucine for nucleotides at positions 352 to 354 of the nucleotide sequence set forth in SEQ ID NO: 2.

In the DNA (b), the identity with the nucleotide sequence set forth in SEQ ID NO: 2 is preferably 70% or more, more preferably 75% or more, further preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of TE activity.

Further, the DNA (b) is also preferably a DNA in which 1 or several (for example 1 or more and 320 or less, preferably 1 or more and 267 or less, more preferably 1 or more and 213 or less, further preferably 1 or more and 160 or less, further preferably 1 or more and 106 or less, further preferably 1 or more and 85 or less, further preferably 1 or more and 74 or less, further preferably 1 or more and 64 or less, further preferably 1 or more and 53 or less, further preferably 1 or more and 42 or less, further preferably 1 or more and 32 or less, further preferably 1 or more and 21 or less, and furthermore preferably 1 or more and 10 or less) nucleotides are deleted, substituted, inserted or added to the nucleotide sequence set forth in SEQ ID NO: 2, and encoding the protein (A) or (B) having TE activity. Further, these nucleotide mutations are different with the nucleotide substitutions of the (b-1) to (b-11).

Furthermore, the DNA (b) is also preferably a DNA capable of hybridizing with a DNA consisting of the nucleotide sequence complementary with the DNA (a) under a stringent condition, and encoding the protein (A) or (B) having TE activity.

The DNA (b) preferably has at least one nucleotide substitution selected from the group consisting of the following (e-1) to (e-8), in addition to at least one nucleotide substitution selected from the group consisting of the (b-1) to (b-11). In the present invention, the DNA (b) more preferably has the nucleotide substitution of (b-1) and at least one nucleotide substitution selected from the group consisting of the following (e-1) to (e-8).
(e-1) substitution of nucleotides encoding isoleucine for nucleotides at a position corresponding to position 316 to 318 of the nucleotide sequence set forth in SEQ ID NO: 2;
(e-2) substitution of nucleotides encoding lysine for nucleotides at a position corresponding to position 322 to 324 of the nucleotide sequence set forth in SEQ ID NO: 2;
(e-3) substitution of nucleotides encoding arginine for nucleotides at a position corresponding to position 322 to 324 of the nucleotide sequence set forth in SEQ ID NO: 2;
(e-4) substitution of nucleotides encoding isoleucine for nucleotides at a position corresponding to position 328 to 330 of the nucleotide sequence set forth in SEQ ID NO: 2;
(e-5) substitution of nucleotides encoding methionine for nucleotides at a position corresponding to position 328 to 330 of the nucleotide sequence set forth in SEQ ID NO: 2;
(e-6) substitution of nucleotides encoding leucine for nucleotides at a position corresponding to position 328 to 330 of the nucleotide sequence set forth in SEQ ID NO: 2;
(e-7) substitution of nucleotides encoding phenylalanine for nucleotides at a position corresponding to position 328 to 330 of the nucleotide sequence set forth in SEQ ID NO: 2; and
(e-8) substitution of nucleotides encoding isoleucine for nucleotides at a position corresponding to position 352 to 354 of the nucleotide sequence set forth in SEQ ID NO: 2.

In the present invention, the DNA (b) preferably has the nucleotide substitution selected from the group consisting of the following (b-1_e-1) to (b-1_e-8):
(b-1_e-1) substitutions of nucleotides encoding isoleucine for nucleotides at a position corresponding to position 769 to 771, and nucleotides encoding isoleucine for nucleotides at a position corresponding to position 316 to 318 of the nucleotide sequence set forth in SEQ ID NO: 2;
(b-1_e-2) substitutions of nucleotides encoding isoleucine for nucleotides at a position corresponding to position 769 to 771, and nucleotides encoding lysine for nucleotides at a position corresponding to position 322 to 324 of the nucleotide sequence set forth in SEQ ID NO: 2;
(b-1_e-3) substitutions of nucleotides encoding isoleucine for nucleotides at a position corresponding to position 769 to 771, and nucleotides encoding arginine for nucleotides at a position corresponding to position 322 to 324 of the nucleotide sequence set forth in SEQ ID NO: 2;
(b-1_e-4) substitutions of nucleotides encoding isoleucine for nucleotides at a position corresponding to position 769 to 771, and nucleotides encoding isoleucine for nucleotides at a position corresponding to position 328 to 330 of the nucleotide sequence set forth in SEQ ID NO: 2;
(b-1_e-5) substitutions of nucleotides encoding isoleucine for nucleotides at a position corresponding to position 769 to 771, and nucleotides encoding methionine for nucleotides at a position corresponding to position 328 to 330 of the nucleotide sequence set forth in SEQ ID NO: 2;
(b-1_e-6) substitutions of nucleotides encoding isoleucine for nucleotides at a position corresponding to position 769 to 771, and nucleotides encoding leucine for nucleotides at a position corresponding to position 328 to 330 of the nucleotide sequence set forth in SEQ ID NO: 2;
(b-1_e-7) substitutions of nucleotides encoding isoleucine for nucleotides at a position corresponding to position 769 to 771, and nucleotides encoding phenylalanine for nucleotides at a position corresponding to position 328 to 330 of the nucleotide sequence set forth in SEQ ID NO: 2; and
(b-1_e-8) substitutions of nucleotides encoding isoleucine for nucleotides at a position corresponding to position 769 to 771, and nucleotides encoding isoleucine for nucleotides at a position corresponding to position 352 to 354 of the nucleotide sequence set forth in SEQ ID NO: 2.

The DNA (c) contains the nucleotide sequence of the DNA (a) or (b) as a part of the nucleotide sequence thereof, and encodes a protein having TE activity. Further, the nucleotide sequence at 5' end of the DNA (c) is preferably a start codon encoding methionine (ATG) or leucine (TTG).

In the nucleotide sequence of the DNA (c), a nucleotide sequence other than the nucleotide sequence of the DNA (a) or (b) can be appropriately selected within the range in which the advantageous effects of the present invention are not adversely affected. The examples thereof include an arbitrary nucleotide sequence of $1^{st}$ to $171^{st}$ nucleotides set forth in SEQ ID NO: 49, and a nucleotide sequence in which 1 or several (preferably 1 or more and 60 or less, more preferably 1 or more and 45 or less, further preferably 1 or more and 30 or less, furthermore preferably 1 or more and 15 or less, and furthermore preferably 1 or more and 9 or less) mutations are introduced into the nucleotide sequence, and the like. The examples of the mutation include deletion, substitution, insertion and addition of nucleotides. These sequences are preferably added to the 5' end side of the nucleotide sequence of the DNA (a) or (b).

Alternatively, the DNA (c) may be a DNA consisting of the nucleotide sequence in which a portion on the 5' end side is deleted in an arbitrary position of the $4^{th}$ to $171^{st}$ nucleotides of the nucleotide sequence set forth in SEQ ID NO: 49 in the amino acid sequence set forth in SEQ ID NO: 49. Moreover, a nucleotide sequence encoding a signal peptide involved in transport or secretion of the protein is preferably added to the 5' end side of the nucleotide sequence of DNA (a) or (b).

A method of introducing the mutation such as deletion, substitution, addition, and insertion into a nucleotide sequence includes, for example, a method of introducing a site-specific mutation. Specific examples of the method of introducing the site-specific mutation include a method of utilizing the Splicing overlap extension (SOE)-PCR (Gene, 1989, vol. 77, p. 61-68), the ODA method (Gene, 1995, 152, 271-276), and the Kunkel method (Proc. Natl. Acad. Sci. USA, 1985, vol. 82, p. 488). Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

A gene encoding the CpTE variant (CpTE variant gene) can be obtained by genetic engineering techniques that are ordinarily carried out. For example, the CpTE variant gene can be artificially synthesized based on the amino acid sequence set forth in SEQ ID NO: 1 or the nucleotide sequence set forth in SEQ ID NO: 2. Further, the CpTE variant gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)].

The transformant of the present invention can be prepared by introducing the CpTE variant gene into a host according to an ordinarily method. Specifically, the transformant can be produced by preparing a recombinant vector or a gene expression cassette which is capable of expressing the CpTE variant gene in a host cell, introducing this vector or cassette into a host cell, and thereby transforming the host cell.

The host for the transformant can be appropriately selected from ordinarily used hosts. For example, microorganisms (including algae and microalgae), plants or animals can be used as the host in the present invention.

As the microorganisms, prokaryotes and eukaryotes can be used, and microorganisms belonging to the genus *Escherichia*, microorganisms belonging to the genus *Bacillus*, microorganisms belonging to the genus *Synechocystis*, cyanobacteria belonging to the genus *Synechococcus*, eukaryotic microorganisms such as yeast and filamentous fungi, or the like can be used. Among these, from a viewpoint of the productivity of lipids, *Escherichia coli*, *Bacillus subtilis*, *Rhodosporidium toruloides*, *Mortierella* sp., or cyanobacteria is preferred, and *Escherichia coli* or cyanobacteria is more preferred.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferred, and algae belonging to the genus *Nannochloropsis* are more preferred. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among these, from a viewpoint of the productivity of lipids, *Nannochloropsis oculata* or *Nannochloropsis gaditana* is preferred, and *Nannochloropsis oculata* is more preferred.

As the plants, from a viewpoint of a high lipid content of seeds, *Arabidopsis thaliana*, *Brassica napus*, *Brassica raga*, *Cocos nucifera*, *Elaeis guineensis*, *cuphea*, *Glycine max*, *Zea mays*, *Oryza sativa*, *Helianthus annuus*, *Cinnamomum camphora*, or *Jatropha curcas* is preferred, and *Arabidopsis thaliana* is more preferred.

From the viewpoints of production efficiency and the usability of lipids to be obtained, microorganisms are preferable, and *Escherichia coli* or cyanobacteria are more preferable as a host.

Cyanobacteria (blue-green bacteria), which can be preferably used in the present invention, belong to a group of eubacteria, and have an ability to produce oxygen through photosynthesis and fix carbon dioxide. Cyanobacteria are one group of prokaryotes that perform photosynthesis using chlorophyll. Cyanobacteria are highly diversified. In view of cell morphology, there are bacteria having a unicellular shape such as *Synechocystis* sp. PCC6803, bacteria having a filamentous shape formed of many cells connected like a string such as *Anabaena* sp. PCC7120 forming heterocysts and fixing nitrogen, bacteria having a spiral shape and a branched shape, and the like. In view of growth environment, there are species adapted in various conditions including thermophilic bacteria such as *Thermosynechococcus elongatus* BP-1 isolated from Beppu Onsen; and oceanic bacteria such as *Synechococcus* sp. CC9311 living in the coast or *Synechococcus* sp. WH8102 living in the outer sea. As bacteria having feature intrinsic to the species, *Microcystis aeruginosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are also mentioned. In cyanobacteria, carbon dioxide fixed by photosynthesis is converted into acetyl-CoA via a large number of enzymatic reaction processes.

Every kind of cyanobacteria can be used in the present invention. Specific examples of the cyanobacteria include cyanobacteria of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*. Among these, cyanobacteria of the genus *Synechocystis*, the genus *Synechococcus*, the genus *Thermosynechococcus*, or the genus *Anabaena* are preferable, and cyanobacteria of the genus *Synechocystis* or the genus *Synechococcus* are more preferable. Further, the host used in the present invention is preferably *Synechocystis* sp. PCC6803, *Synechocystis* sp. PCC7509, *Synechocystis* sp. PCC6714, *Synechococcus elongatus* sp. PCC7942, *Thermosynechococcus elongatus* BP-1, *Trichodesmium erythraeum* IMS101, *Acaryochloris mariana* MBIC11017, *Crocosphaera watsonii* WH8501, or *Anabaena* sp. PCC7120, more preferably *Synechocystis* sp. PCC6803 or *Synechococcus elongatus* sp. PCC7942, and further preferably *Synechococcus elongatus* sp. PCC7942.

Further in cyanobacteria, a function of acyl-ACP synthetase (hereinafter, also referred to as "aas") is preferably lost. In a case of using cyanobacteria wherein the function of aas is lost, ability to secrete the lipid produced by the transformant can be improved. Herein, "aas" means one kind of enzyme related to fatty acid synthesis, and has a function of forming a thioester bond in an ATP-dependent manner by using the free fatty acids and an ACP protein as the substrate to produce acyl-ACP. Accumulation and secretion of fatty acids are known to be promoted by causing loss of the function of aas in cyanobacteria (see Plant Physiology, 2010, vol. 152(3), pp. 1598-1610).

A vector for use as the plasmid for gene expression or a vector containing the gene expression cassette (plasmid) may be any vector capable of introducing the gene encoding the target protein into a host, and expressing the target gene in the host cell. For example, a vector which has expression regulation regions such as a promoter and a terminator in accordance with the type of the host to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (1986, Plasmid 15(2), p. 93-103), pBR322 (manufactured by Takara Bio), pRS403 (manufactured by Stratagene), pMW218/219 (manufactured by Nippon Gene), a pRI-based vector (manufactured by Takara Bio), a pBI-based vector (manufactured by Clontech), and an IN3-based vector (manufactured by Inplanta Innovations Inc.). In particular, in the case of using *Escherichia coli* as the host, pBluescript II SK(−) or pMW218/219 is preferably used. Further, in the case of using cyanobacteria as the host, a pUC-based vector is preferably used.

When the algae or the microalgae are used as the host, specific examples of the vector include pUC19 (manufactured by Takara Bio), P66 (Chlamydomonas Center), P-322 (Chlamydomonas Center), pPha-T1 (see Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Proceedings of the National Academy of Sciences of the United States of America, 2011, vol. 108(52), by using the DNA fragment (gene expression cassette) consisting of the target gene, a promoter and a terminator.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Specific examples of this DNA fragment include a DNA fragment amplified by PCR method, and a restriction enzyme-cut DNA fragment. Introduction of the gene encoding a target protein to the vector can be conducted by an ordinary technique such as restriction enzyme treatment and ligation.

A kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, plant-derived Rubisco promoter, a promoter of a violaxanthin/(chlorophyll a)-binding protein gene derived from the genus *Nannochloropsis* (VCP1 promoter, VCP2 promoter) (Proceedings of the National Academy of Sciences of the United States of America, 2011, vol. 108(52)), a promoter of an oleosin-like protein LDSP (lipid droplet surface protein) gene derived from the genus *Nannochloropsis* (PLOS Genetics, 2012, vol. 8(11): e1003064. DOI: 10.1371), and a promoter of an rrnA operon gene encoding a ribosomal RNA.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

The method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using Agrobacterium, a particle gun method, and the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

The CpTE variant gene to be introduced into each of hosts is preferably optimized in codon in accordance with use frequency of codon in the host to be used. Information of codons used in each of organisms is available from Codon Usage Database (www.kazusa.or.jp/codon/).

In the transformant of the present invention, the productivity of medium-chain fatty acids or lipids containing the same as components, especially a proportion of medium-chain fatty acids or lipids containing the same as components in the total fatty acids or lipids to be produced is significantly improved, in comparison with that in a wild type itself. Moreover, as a result, in the transformant of the present invention, the fatty acid composition in the lipid to be produced is modified. Therefore, the transformant of the present invention can be preferably applied to production of fatty acids having specific number of carbon atoms or lipids containing the same as components, particularly medium-chain fatty acids or lipids containing the same as components, preferably fatty acids having 8 or more and 10 or less carbon atoms or lipids containing the same as components, more preferably fatty acids having 8 or 10 carbon atoms or lipids containing the same as components, further preferably saturated fatty acids having 8 or 10 carbon atoms (caprylic acid or capric acid) or lipids containing the same as components.

Hereinafter, in the present specification, a cell into which a gene encoding at least one protein selected from the group consisting of the proteins (A) to (C) is introduced is also referred to as the "transformant". On the other hand, a cell into which a gene encoding at least one protein selected from the group consisting of the proteins (A) to (C) is not introduced is also referred to as the "host" or "wild type strain".

In the transformant of the present invention, productivity of medium-chain fatty acids or lipids containing the same as components is improved in comparison with that in the host in which expression of any one of the proteins (A) to (C) is not enhanced. Accordingly, if the transformant of the present invention is cultured under suitable conditions and then the medium-chain fatty acids or the lipids containing the same as components are collected from an obtained cultured product or an obtained growth product, the medium-chain fatty acids or the lipids containing the same as components can be efficiently produced. Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of fatty acids, for example, precursor substances involved in the fatty acid biosynthesis system, such as glycerol, acetic acid or glucose, may be added to the medium.

For example, in the case of using *Escherichia coli* as the host, culturing of *Escherichia coli* may be carried out in LB medium or Overnight Express Instant TB Medium (Novagen) at 30 to 37° C. for half a day to 1 day.

In the case of using cyanobacteria as the hosts, culturing thereof may be carried out, according to liquid culture or a modified method thereof, by using a medium to be ordinarily used for culture of cyanobacteria, such as a BG-11 medium (J. Gen. Microbial., 1979, vol. 111, p. 1-61), an A medium (Proc. Natl. Acad. Sci. U.S.A., 1980, vol. 77, p. 6052-6056) and an AA medium (Plant Physiol., 1955, vol. 30, p. 366-372). The culture for producing lipid may be performed in a period during which bacterial cells are sufficiently grown to accumulate fatty acids in high concentrations, for example, from 7 to 45 days, preferably from 10 to 30 days, and more preferably from 14 to 21 days, by an aeration/spinner culture or shaking culture.

In the case of using *Arabidopsis* as the host, for example, growth of *Arabidopsis* may be carried out at soil under the temperature conditions of 20 to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the algae to be seeded to the culture medium is appropriately selected. In view of viability, the amount is preferably 1% (vol/vol) or more, per culture medium. The upper limit thereof is preferably 50% (vol/vol) or less, and more preferably 10% (vol/vol) or less. The range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10° C. or more, and more preferably 15° C. or more. The upper limit thereof is preferably 35° C. or less, and more preferably 30° C. or less. The range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably 100 lx or more, more preferably 300 lx or more, and further preferably 1,000 lx or more. The upper limit thereof is preferably 50,000 lx or less, more preferably 10,000 lx or less, and further preferably 6,000 lx or less. The range of irradiance during the light irradiation is preferably 100 to 50,000 lx, more preferably 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 hours or more, and more preferably 10 hours or more. The upper limit thereof is preferably 24 hours or less, and more preferably 18 hours or less. The range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably 0.03% (which is the same degree as the concentration under atmospheric conditions) or more, more preferably 0.05% or more, further preferably 0.1% or more, and furthermore preferably 0.3% or more. The upper limit thereof is preferably 10% or less, more preferably 5% or less, further preferably 3% or less, and furthermore preferably 1% or less. The range of the concentration of carbon dioxide is preferably from 0.03 to 10%, more preferably from 0.05 to 5%, further preferably from 0.1 to 3%, and furthermore preferably from 0.3 to 1%. A concentration of carbonate is not particularly When sodium hydrogen carbonate is used, for example, from viewpoints of the growth promotion and the improvement in the productivity of fatty acids, the concentration is preferably 0.01% by mass or more, more preferably 0.05% by mass or more, and further preferably 0.1% by mass or more. The upper limit thereof is preferably 5% by mass or less, more preferably 2% by mass or less, and further preferably 1% by mass or less. The range of the concentration of sodium hydrogen carbonate is preferably from 0.01 to 5% by mass, more preferably from 0.05 to 2% by mass, and further preferably from 0.1 to 1% by mass.

Culture time is not particularly limited, and the culture may be performed for a long time (for example, about 150 days) so that an alga body in which the lipids are accumulated at a high concentration can grow at a high concentration. The culture time is preferably 3 days or more, and more preferably 7 days or more. The upper limit thereof is preferably 90 days or less, and more preferably 30 days or less. The range of the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture or shaking culture is preferred, and aerated and agitated culture is more preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scale culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

Moreover, in the case of using a transformant prepared by using, as a host, *Escherichia coli* prepared by causing loss of the function of a β-oxidation pathway being a fatty acid degradation pathway, or cyanobacteria prepared by causing loss of the function of aas, produced lipids are secreted to the outside of cells. Therefore, it is unnecessary to destroy bacterial cells in order to collect lipid, and the cells remaining after collecting the lipid can be repeatedly used for production of the lipid.

The lipids produced in the production method of the present invention preferably contain fatty acids or fatty acid compounds, and more preferably contain fatty acids or fatty acid ester compounds, in view of usability thereof. The fatty acid ester compound is preferably at least one kind selected from the group consisting of MAG, DAG, and TAG, and more preferably TAG.

In view of usability for a surfactant or the like, and from a nutritional viewpoint, the fatty acid or the ester compound thereof contained in the lipid is preferably a medium-chain fatty acid or an ester compound thereof. Specifically, the fatty acid or the ester compound thereof contained in the lipid is preferably a fatty acid having 8 or more and 10 or less carbon atoms or an ester compound thereof, more preferably a fatty acid having 8 or 10 carbon atoms or an ester compound thereof, more preferably a saturated fatty acid having 8 or 10 carbon atoms (caprylic acid or capric acid) or an ester compound thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of modifying fatty acid composition of lipids to be produced, proteins, genes, recombinant vectors or DNA cassettes, transformants and methods of preparing the same, described below.

<1> A method of producing lipids, containing the steps of:
culturing a transformant into which a gene encoding at least one protein selected from the group consisting of the following proteins (A) to (C) is introduced; and
producing fatty acids or lipids containing the same as components:
(A) a protein consisting of an amino acid sequence having at least one amino acid substitution selected from the group consisting of the following (A-1) to (A-11), preferably the amino acid substitution of (A-1) in the amino acid sequence set forth in SEQ ID NO: 1, and having TE activity;
(B) a protein consisting of an amino acid sequence having at least one amino acid substitution selected from the group consisting of the following (B-1) to (B-11) in an amino acid sequence having 85% or more, preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the amino acid sequence set forth in SEQ ID NO: 1, and having TE activity; and
(C) a protein containing the amino acid sequence of the protein (A) or (B) (preferably the amino acid sequence of the protein (A) or (B) except for a synthesis initiation codon), and having TE activity:
(A-1) substitution of isoleucine for leucine at position 257 of the amino acid sequence set forth in SEQ ID NO: 1;
(A-2) substitution of arginine for threonine at position 251 of the amino acid sequence set forth in SEQ ID NO: 1;
(A-3) substitution of lysine for threonine at position 251 of the amino acid sequence set forth in SEQ ID NO: 1;
(A-4) substitution of histidine for threonine at position 251 of the amino acid sequence set forth in SEQ ID NO: 1;
(A-5) substitution of isoleucine for tryptophan at position 254 of the amino acid sequence set forth in SEQ ID NO: 1;
(A-6) substitution of tyrosine for tryptophan at position 254 of the amino acid sequence set forth in SEQ ID NO: 1;
(A-7) substitution of methionine for leucine at position 257 of the amino acid sequence set forth in SEQ ID NO: 1;
(A-8) substitution of valine for leucine at position 257 of the amino acid sequence set forth in SEQ ID NO: 1;
(A-9) substitution of phenylalanine for leucine at position 257 of the amino acid sequence set forth in SEQ ID NO: 1;
(A-10) substitution of cysteine for valine at position 266 of the amino acid sequence set forth in SEQ ID NO: 1;
(A-11) substitution of tyrosine for tryptophan at position 271 of the amino acid sequence set forth in SEQ ID NO: 1;
(B-1) substitution of isoleucine for an amino acid at a position corresponding to position 257 (preferably or generally, leucine) of the amino acid sequence set forth in SEQ ID NO: 1;
(B-2) substitution of arginine for an amino acid at a position corresponding to position 251 (preferably or generally, threonine) of the amino acid sequence set forth in SEQ ID NO: 1;
(B-3) substitution of lysine for an amino acid at a position corresponding to position 251 (preferably or generally, threonine) of the amino acid sequence set forth in SEQ ID NO: 1;
(B-4) substitution of histidine for an amino acid at a position corresponding to position 251 (preferably or generally, threonine) of the amino acid sequence set forth in SEQ ID NO: 1;
(B-5) substitution of isoleucine for an amino acid at a position corresponding to position 254 (preferably or generally, tryptophan) of the amino acid sequence set forth in SEQ ID NO: 1;
(B-6) substitution of tyrosine for an amino acid at a position corresponding to position 254 (preferably or generally, tryptophan) of the amino acid sequence set forth in SEQ ID NO: 1;
(B-7) substitution of methionine for an amino acid at a position corresponding to position 257 (preferably or generally, leucine) of the amino acid sequence set forth in SEQ ID NO: 1;
(B-8) substitution of valine for an amino acid at a position corresponding to position 257 (preferably or generally, leucine) of the amino acid sequence set forth in SEQ ID NO: 1;
(B-9) substitution of phenylalanine for an amino acid at a position corresponding to position 257 (preferably or generally, leucine) of the amino acid sequence set forth in SEQ ID NO: 1;
(B-10) substitution of cysteine for an amino acid at a position corresponding to position 266 (preferably or generally, valine) of the amino acid sequence set forth in SEQ ID NO: 1; and
(B-11) substitution of tyrosine for an amino acid at a position corresponding to position 271 (preferably or generally, tryptophan) of the amino acid sequence set forth in SEQ ID NO: 1.

<2> A method of producing lipids, containing the steps of:
culturing a transformant into which a gene encoding at least one protein selected from the group consisting of the proteins (A) to (C) is introduced; and
improving productivity of medium-chain fatty acids or lipids containing the same as components to be produced in a cell of the transformant.

<3> A method of modifying fatty acid composition, containing the steps of:
culturing a transformant into which a gene encoding at least one protein selected from the group consisting of the proteins (A) to (C) is introduced; and
increasing a proportion of medium-chain fatty acids in the whole fatty acids to be produced in a cell of the transformant.

<4> The method described in any one of the above items <1> to <3>, wherein the protein (B) is a protein in which 1 or several amino acids, for example preferably 1 or more and 53 or less amino acids, more preferably 1 or more and 35 or less amino acids, further preferably 1 or more and 28 or less amino acids, furthermore preferably 1 or more and 24 or less amino acids, furthermore preferably 1 or more and 21 or less amino acids, furthermore preferably 1 or more and 17 or less amino acids, furthermore preferably 1 or more and 14 or less amino acids, furthermore preferably 1 or more and 10 or less amino acids, furthermore preferably 1 or more and 7 or less amino acids, and furthermore preferably 1 or more and 3 or less amino acids, are deleted, substituted, inserted or added to the amino acid sequence of the protein (A), and having at least one amino acid substitution selected from the group consisting of the (B-1) to (B-11), preferably the amino acid substitution of (B-1).

<5> The method described in any one of the above items <1> to <4>, wherein the protein (A) has at least one amino acid substitution selected from the group consisting of the following (D-1) to (D-8) (preferably the amino acid substitution of (A-1) and at least one amino acid substitution selected from the group consisting of the following (D-1) to (D-8)), and the protein (B) has at least one amino acid substitution selected from the group consisting of the following (E-1) to (E-8) (preferably the amino acid substitution of (B-1) and at least one amino acid substitution selected from the group consisting of the following (E-1) to (E-8)):

(D-1) substitution of isoleucine for valine at position 106 of the amino acid sequence set forth in SEQ ID NO: 1;
(D-2) substitution of lysine for asparagine at position 108 of the amino acid sequence set forth in SEQ ID NO: 1;
(D-3) substitution of arginine for asparagine at position 108 of the amino acid sequence set forth in SEQ ID NO: 1;
(D-4) substitution of isoleucine for valine at position 110 of the amino acid sequence set forth in SEQ ID NO: 1;
(D-5) substitution of methionine for valine at position 110 of the amino acid sequence set forth in SEQ ID NO: 1;
(D-6) substitution of leucine for valine at position 110 of the amino acid sequence set forth in SEQ ID NO: 1;
(D-7) substitution of phenylalanine for valine at position 110 of the amino acid sequence set forth in SEQ ID NO: 1;
(D-8) substitution of isoleucine for cysteine at position 118 of the amino acid sequence set forth in SEQ ID NO: 1;
(E-1) substitution of isoleucine for an amino acid at a position corresponding to position 106 (preferably or generally, valine) of the amino acid sequence set forth in SEQ ID NO: 1;
(E-2) substitution of lysine for an amino acid at a position corresponding to position 108 (preferably or generally, asparagine) of the amino acid sequence set forth in SEQ ID NO: 1;
(E-3) substitution of arginine for an amino acid at a position corresponding to position 108 (preferably or generally, asparagine) of the amino acid sequence set forth in SEQ ID NO: 1;
(E-4) substitution of isoleucine for an amino acid at a position corresponding to position 110 (preferably or generally, valine) of the amino acid sequence set forth in SEQ ID NO: 1;
(E-5) substitution of methionine for an amino acid at a position corresponding to position 110 (preferably or generally, valine) of the amino acid sequence set forth in SEQ ID NO: 1;
(E-6) substitution of leucine for an amino acid at a position corresponding to position 110 (preferably or generally, valine) of the amino acid sequence set forth in SEQ ID NO: 1;
(E-7) substitution of phenylalanine for an amino acid at a position corresponding to position 110 (preferably or generally, valine) of the amino acid sequence set forth in SEQ ID NO: 1; and
(E-8) substitution of isoleucine for an amino acid at a position corresponding to position 118 (preferably or generally, cysteine) of the amino acid sequence set forth in SEQ ID NO: 1.

<6> The method described in any one of the above items <1> to <5>, wherein the protein (A) has amino acid substitutions selected from the group consisting of the following (A-1_D-1) to (A-1_D-8), and the protein (B) has amino acid substitutions selected from the group consisting of the following (B-1_E-1) to (B-1_E-8):

(A-1_D-1) substitutions of isoleucine for leucine at position 257, and isoleucine for valine at position 106 of the amino acid sequence set forth in SEQ ID NO: 1;
(A-1_D-2) substitutions of isoleucine for leucine at position 257, and lysine for asparagine at position 108 of the amino acid sequence set forth in SEQ ID NO: 1;
(A-1_D-3) substitutions of isoleucine for leucine at position 257, and arginine for asparagine at position 108 of the amino acid sequence set forth in SEQ ID NO: 1;
(A-1_D-4) substitutions of isoleucine for leucine at position 257, and isoleucine for valine at position 110 of the amino acid sequence set forth in SEQ ID NO: 1;
(A-1_D-5) substitutions of isoleucine for leucine at position 257, and methionine for valine at position 110 of the amino acid sequence set forth in SEQ ID NO: 1;
(A-1_D-6) substitutions of isoleucine for leucine at position 257, and leucine for valine at position 110 of the amino acid sequence set forth in SEQ ID NO: 1; SEQ
(A-1_D-7) substitutions of isoleucine for leucine at position 257, and phenylalanine for valine at position 110 of the amino acid sequence set forth in SEQ ID NO: 1;
(A-1_D-8) substitutions of isoleucine for leucine at position 257, and isoleucine for cysteine at position 118 of the amino acid sequence set forth in SEQ ID NO: 1;
(B-1_E-1) substitutions of isoleucine for an amino acid at a position corresponding to position 257 (preferably or generally, leucine), and isoleucine for an amino acid at a position corresponding to position 106 (preferably or generally, valine) of the amino acid sequence set forth in SEQ ID NO: 1;
(B-1_E-2) substitutions of isoleucine for an amino acid at a position corresponding to position 257 (preferably or generally, leucine), and lysine for an amino acid at a position corresponding to position 108 (preferably or generally, asparagine) of the amino acid sequence set forth in SEQ ID NO: 1;
(B-1_E-3) substitutions of isoleucine for an amino acid at a position corresponding to position 257 (preferably or generally, leucine), and arginine for an amino acid at a position corresponding to position 108 (preferably or generally, asparagine) of the amino acid sequence set forth in SEQ ID NO: 1;
(B-1_E-4) substitutions of isoleucine for an amino acid at a position corresponding to position 257 (preferably or generally, leucine), and isoleucine for an amino acid at a position corresponding to position 110 (preferably or generally, valine) of the amino acid sequence set forth in SEQ ID NO: 1;
(B-1_E-5) substitutions of isoleucine for an amino acid at a position corresponding to position 257 (preferably or generally, leucine), and methionine for an amino acid at a position corresponding to position 110 (preferably or generally, valine) of the amino acid sequence set forth in SEQ ID NO: 1;
(B-1_E-6) substitutions of isoleucine for an amino acid at a position corresponding to position 257 (preferably or generally, leucine), and leucine for an amino acid at a position corresponding to position 110 (preferably or generally, valine) of the amino acid sequence set forth in SEQ ID NO: 1;
(B-1_E-7) substitutions of isoleucine for an amino acid at a position corresponding to position 257 (preferably or generally, leucine), and phenylalanine for an amino acid at a position corresponding to position 110 (preferably or generally, valine) of the amino acid sequence set forth in SEQ ID NO: 1; and
(B-1_E-8) substitutions of isoleucine for an amino acid at a position corresponding to position 257 (preferably or generally, leucine), and isoleucine for an amino acid at a position corresponding to position 118 (preferably or generally, cysteine) of the amino acid sequence set forth in SEQ ID NO: 1.

<7> The method described in any one of the above items <1> to <6>, wherein a gene encoding at least one protein selected from the group consisting of the proteins (A) to (C) is a gene consisting of any one of the following DNAs (a) to (c):
(a) a DNA consisting of a nucleotide sequence having at least one nucleotide substitution selected from the group consisting of the following (a-1) to (a-11), preferably the nucleotide substitution of (a-1) in the nucleotide sequence set forth in SEQ ID NO: 2, and encoding a protein having TE activity;
(b) a DNA consisting of a nucleotide sequence having at least one nucleotide substitution selected from the group consisting of the following (b-1) to (b-11), preferably the nucleotide substitution of (b-1) in a nucleotide sequence having 70% or more, preferably 75% or more, more preferably 80% or more, more preferably 85% or more, more preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the nucleotide sequence set forth in SEQ ID NO: 2, and encoding a protein having TE activity; and
(c) a DNA containing the nucleotide sequence of the DNA (a) or (b) (preferably, a nucleotide sequence of the DNA (a) or (b) except for the start codon), and encoding a protein having TE activity:
(a-1) substitution of nucleotides encoding isoleucine for nucleotides at positions 769 to 771 of the nucleotide sequence set forth in SEQ ID NO: 2;
(a-2) substitution of nucleotides encoding arginine for nucleotides at positions 751 to 753 of the nucleotide sequence set forth in SEQ ID NO: 2;
(a-3) substitution of nucleotides encoding lysine for nucleotides at positions 751 to 753 of the nucleotide sequence set forth in SEQ ID NO: 2
(a-4) substitution of nucleotides encoding histidine for nucleotides at positions 751 to 753 of the nucleotide sequence set forth in SEQ ID NO: 2;
(a-5) substitution of nucleotides encoding isoleucine for nucleotides at positions 760 to 762 of the nucleotide sequence set forth in SEQ ID NO: 2;
(a-6) substitution of nucleotides encoding tyrosine for nucleotides at positions 760 to 762 of the nucleotide sequence set forth in SEQ ID NO: 2;
(a-7) substitution of nucleotides encoding methionine for nucleotides at positions 769 to 771 of the nucleotide sequence set forth in SEQ ID NO: 2;
(a-8) substitution of nucleotides encoding valine for nucleotides at positions 769 to 771 of the nucleotide sequence set forth in SEQ ID NO: 2;
(a-9) substitution of nucleotides encoding phenylalanine for nucleotides at positions 769 to 771 of the nucleotide sequence set forth in SEQ ID NO: 2;
(a-10) substitution of nucleotides encoding cysteine for nucleotides at positions 796 to 798 of the nucleotide sequence set forth in SEQ ID NO: 2;
(a-11) substitution of nucleotides encoding tyrosine for nucleotides at positions 811 to 813 of the nucleotide sequence set forth in SEQ ID NO: 2;
(b-1) substitution of nucleotides encoding isoleucine for nucleotides at positions corresponding to positions 769 to 771 of the nucleotide sequence set forth in SEQ ID NO: 2;
(b-2) substitution of nucleotides encoding arginine for nucleotides at positions corresponding to positions 751 to 753 of the nucleotide sequence set forth in SEQ ID NO: 2;
(b-3) substitution of nucleotides encoding lysine for nucleotides at positions corresponding to positions 751 to 753 of the nucleotide sequence set forth in SEQ ID NO: 2;
(b-4) substitution of nucleotides encoding histidine for nucleotides at positions corresponding to positions 751 to 753 of the nucleotide sequence set forth in SEQ ID NO: 2;
(b-5) substitution of nucleotides encoding isoleucine for nucleotides at positions corresponding to positions 760 to 762 of the nucleotide sequence set forth in SEQ ID NO: 2;
(b-6) substitution of nucleotides encoding tyrosine for nucleotides at positions corresponding to positions 760 to 762 of the nucleotide sequence set forth in SEQ ID NO: 2;
(b-7) substitution of nucleotides encoding methionine for nucleotides at positions corresponding to positions 769 to 771 of the nucleotide sequence set forth in SEQ ID NO: 2;
(b-8) substitution of nucleotides encoding valine for nucleotides at positions corresponding to positions 769 to 771 of the nucleotide sequence set forth in SEQ ID NO: 2;
(b-9) substitution of nucleotides encoding phenylalanine for nucleotides at positions corresponding to positions 769 to 771 of the nucleotide sequence set forth in SEQ ID NO: 2;
(b-10) substitution of nucleotides encoding cysteine for nucleotides at positions corresponding to positions 796 to 798 of the nucleotide sequence set forth in SEQ ID NO: 2; and
(b-11) substitution of nucleotides encoding tyrosine for nucleotides at positions corresponding to positions 811 to 813 of the nucleotide sequence set forth in SEQ ID NO: 2.
<8> The method described in the above item <7>, wherein the DNA (b) is a DNA consisting of a nucleotide sequence in which 1 or several nucleotides, preferably 1 or more and 320 or less nucleotides, more preferably 1 or more and 267 or less nucleotides, further preferably 1 or more and 213 or less nucleotides, furthermore preferably 1 or more and 160 or less nucleotides, furthermore preferably 1 or more and 106 or less nucleotides, furthermore preferably 1 or more and 85 or less nucleotides, furthermore preferably 1 or more and 74 or less nucleotides, furthermore preferably 1 or more and 64 or less nucleotides, furthermore preferably 1 or more and 53 or less nucleotides, furthermore preferably 1 or more and 42 or less nucleotides, furthermore preferably 1 or more and 32 or less nucleotides, furthermore preferably 1 or more and 21 or less nucleotides, and furthermore preferably 1 or more and 10 or less nucleotides, are deleted, substituted, inserted or added to the nucleotide sequence of the DNA (a), having at least one nucleotide substitution selected from the group consisting of the (b-1) to (b-11), preferably the nucleotide substitution of (b-1), and encoding the protein (A) or (B) having TE activity, or a DNA capable of hybridizing with a DNA consisting of a nucleotide sequence complementary with the DNA (a) under a stringent condition, having at least one nucleotide substitution selected from the group consisting of the (b-1) to (b-11), preferably the nucleotide substitution of (b-1), and encoding the protein (A) or (B) having TE activity.
<9> The method described in the above item <7> or <8>, wherein the DNA (a) has at least one nucleotide substitution selected from the group consisting of the following (d-1) to (d-8) (preferably the nucleotide substitution of (a-1) and at least one nucleotide substitution selected from the group consisting of the following (d-1) to (d-8)), and the DNA (b) has at least one nucleotide substitution selected from the group consisting of the following (e-1) to (e-8) (preferably the nucleotide substitution of (b-1) and at least one nucleotide substitution selected from the group consisting of the following (e-1) to (e-8)):

(d-1) substitution of nucleotides encoding isoleucine for nucleotides at positions 316 to 318 of the nucleotide sequence set forth in SEQ ID NO: 2;
(d-2) substitution of nucleotides encoding lysine for nucleotides at positions 322 to 324 of the nucleotide sequence set forth in SEQ ID NO: 2;
(d-3) substitution of nucleotides encoding arginine for nucleotides at positions 322 to 324 of the nucleotide sequence set forth in SEQ ID NO: 2;
(d-4) substitution of nucleotides encoding isoleucine for nucleotides at positions 328 to 330 of the nucleotide sequence set forth in SEQ ID NO: 2;
(d-5) substitution of nucleotides encoding methionine for nucleotides at positions 328 to 330 of the nucleotide sequence set forth in SEQ ID NO: 2;
(d-6) substitution of nucleotides encoding leucine for nucleotides at positions 328 to 330 of the nucleotide sequence set forth in SEQ ID NO: 2;
(d-7) substitution of nucleotides encoding phenylalanine for nucleotides at positions 328 to 330 of the nucleotide sequence set forth in SEQ ID NO: 2;
(d-8) substitution of nucleotides encoding isoleucine for nucleotides at positions 352 to 354 of the nucleotide sequence set forth in SEQ ID NO: 2.
(e-1) substitution of nucleotides encoding isoleucine for nucleotides at positions corresponding to positions 316 to 318 of the nucleotide sequence set forth in SEQ ID NO: 2;
(e-2) substitution of nucleotides encoding lysine for nucleotides at positions corresponding to positions 322 to 324 of the nucleotide sequence set forth in SEQ ID NO: 2;
(e-3) substitution of nucleotides encoding arginine for nucleotides at positions corresponding to positions 322 to 324 of the nucleotide sequence set forth in SEQ ID NO: 2;
(e-4) substitution of nucleotides encoding isoleucine for nucleotides at positions corresponding to positions 328 to 330 of the nucleotide sequence set forth in SEQ ID NO: 2;
(e-5) substitution of nucleotides encoding methionine for nucleotides at positions corresponding to positions 328 to 330 of the nucleotide sequence set forth in SEQ ID NO: 2;
(e-6) substitution of nucleotides encoding leucine for nucleotides at positions corresponding to positions 328 to 330 of the nucleotide sequence set forth in SEQ ID NO: 2;
(e-7) substitution of nucleotides encoding phenylalanine for nucleotides at positions corresponding to positions 328 to 330 of the nucleotide sequence set forth in SEQ ID NO: 2; and
(e-8) substitution of nucleotides encoding isoleucine for nucleotides at positions corresponding to positions 352 to 354 of the nucleotide sequence set forth in SEQ ID NO: 2.
<10> The method described in any one of the above items <7> to <9>, wherein the DNA (a) has nucleotide substitutions selected from the group consisting of the following (a-1_d-1) to (a-1_d-8), and the DNA (b) has nucleotide substitutions selected from the group consisting of the following (b-1_e-1) to (b-1_e-8):
(a-1_d-1) substitutions of nucleotides encoding isoleucine for nucleotides at positions 769 to 771, and nucleotides encoding isoleucine for nucleotides at positions 316 to 318 of the nucleotide sequence set forth in SEQ ID NO: 2;
(a-1_d-2) substitutions of nucleotides encoding isoleucine for nucleotides at positions 769 to 771, and nucleotides encoding lysine for nucleotides at positions 322 to 324 of the nucleotide sequence set forth in SEQ ID NO: 2;
(a-1_d-3) substitutions of nucleotides encoding isoleucine for nucleotides at positions 769 to 771, and nucleotides encoding arginine for nucleotides at positions 322 to 324 of the nucleotide sequence set forth in SEQ ID NO: 2;
(a-1_d-4) substitutions of nucleotides encoding isoleucine for nucleotides at positions 769 to 771, and nucleotides encoding isoleucine for nucleotides at positions 328 to 330 of the nucleotide sequence set forth in SEQ ID NO: 2;
(a-1_d-5) substitutions of nucleotides encoding isoleucine for nucleotides at positions 769 to 771, and nucleotides encoding methionine for nucleotides at positions 328 to 330 of the nucleotide sequence set forth in SEQ ID NO: 2;
(a-1_d-6) substitutions of nucleotides encoding isoleucine for nucleotides at positions 769 to 771, and nucleotides encoding leucine for nucleotides at positions 328 to 330 of the nucleotide sequence set forth in SEQ ID NO: 2;
(a-1_d-7) substitutions of nucleotides encoding isoleucine for nucleotides at positions 769 to 771, and nucleotides encoding phenylalanine for nucleotides at positions 328 to 330 of the nucleotide sequence set forth in SEQ ID NO: 2;
(a-1_d-8) substitutions of nucleotides encoding isoleucine for nucleotides at positions 769 to 771, and nucleotides encoding isoleucine for nucleotides at positions 352 to 354 of the nucleotide sequence set forth in SEQ ID NO: 2;
(b-1_e-1) substitutions of nucleotides encoding isoleucine for nucleotides at positions corresponding to positions 769 to 771, and nucleotides encoding isoleucine for nucleotides at positions corresponding to positions 316 to 318 of the nucleotide sequence set forth in SEQ ID NO: 2;
(b-1_e-2) substitutions of nucleotides encoding isoleucine for nucleotides at positions corresponding to positions 769 to 771, and nucleotides encoding lysine for nucleotides at positions corresponding to positions 322 to 324 of the nucleotide sequence set forth in SEQ ID NO: 2;
(b-1_e-3) substitutions of nucleotides encoding isoleucine for nucleotides at positions corresponding to positions 769 to 771, and nucleotides encoding arginine for nucleotides at positions corresponding to positions 322 to 324 of the nucleotide sequence set forth in SEQ ID NO: 2;
(b-1_e-4) substitutions of nucleotides encoding isoleucine for nucleotides at positions corresponding to positions 769 to 771, and nucleotides encoding isoleucine for nucleotides at positions corresponding to positions 328 to 330 of the nucleotide sequence set forth in SEQ ID NO: 2;
(b-1_e-5) substitutions of nucleotides encoding isoleucine for nucleotides at positions corresponding to positions 769 to 771, and nucleotides encoding methionine for nucleotides at positions corresponding to positions 328 to 330 of the nucleotide sequence set forth in SEQ ID NO: 2;
(b-1_e-6) substitutions of nucleotides encoding isoleucine for nucleotides at positions corresponding to positions 769 to 771, and nucleotides encoding leucine for nucleotides at positions corresponding to positions 328 to 330 of the nucleotide sequence set forth in SEQ ID NO: 2;
(b-1_e-7) substitutions of nucleotides encoding isoleucine for nucleotides at positions corresponding to positions 769 to 771, and nucleotides encoding phenylalanine for nucleotides at positions corresponding to positions 328 to 330 of the nucleotide sequence set forth in SEQ ID NO: 2; and
(b-1_e-8) substitutions of nucleotides encoding isoleucine for nucleotides at positions corresponding to positions 769 to 771, and nucleotides encoding isoleucine for nucleotides at positions corresponding to positions 352 to 354 of the nucleotide sequence set forth in SEQ ID NO: 2.
<11> The method described in any one of the above items <1> to <10>, wherein the transformant is a transformant of microorganism.
<12> The method described in the above item <11>, wherein the microorganism is *Escherichia coli*.
<13> The method described in the above item <11>, wherein the microorganism is cyanobacteria.

<14> The method described in any one of the above items <1> to <13>, wherein the fatty acids or lipids contain a medium-chain fatty acid or a fatty acid ester compound thereof, preferably a fatty acid having 8 or more and 10 or less carbon atoms or a fatty acid ester compound thereof, more preferably a fatty acid having 8 or 10 carbon atoms or a fatty acid ester compound thereof, and more preferably a saturated fatty acid having 8 or 10 carbon atoms (caprylic acid, capric acid) or a fatty acid ester compound thereof.
<15> The proteins (A) to (C).
<16> The protein described in the above item <15>, wherein the protein (A) has at least one amino acid substitution selected from the group consisting of the (D-1) to (D-8) (preferably the amino acid substitution of (A-1) and at least one amino acid substitution selected from the group consisting of the (D-1) to (D-8)), and the protein (B) has at least one amino acid substitution selected from the group consisting of the (E-1) to (E-8) (preferably the amino acid substitution of (B-1) and at least one amino acid substitution selected from the group consisting of the (E-1) to (E-8)).
<17> The protein described in the above item <15> or <16>, wherein the protein (A) has amino acid substitutions selected from the group consisting of the following (A-1_D-1) to (A-1_D-8), and the protein (B) has amino acid substitutions selected from the group consisting of the following (B-1_E-1) to (B-1_E-8).
<18> A gene encoding the protein described in any one of the above items <15> to <17>.
<19> A gene consisting of any one of the DNAs (a) to (c).
<20> The gene described in the above item <19>, wherein the DNA (a) has at least one nucleotide substitution selected from the group consisting of the (d-1) to (d-8) (preferably the nucleotide substitution of (a-1) and at least one nucleotide substitution selected from the group consisting of the (d-1) to (d-8)), and the DNA (b) has at least one nucleotide substitution selected from the group consisting of the (e-1) to (e-8) (preferably the nucleotide substitution of (b-1) and at least one nucleotide substitution selected from the group consisting of the (e-1) to (e-8)).
<21> The gene described in the above items <19> or <20>, wherein the DNA (a) has nucleotide substitutions selected from the group consisting of the (a-1_d-1) to (a-1_d-8), and the DNA (b) has nucleotide substitutions selected from the group consisting of the (b-1_e-1) to (b-1_e-8).
<22> A recombinant vector or a DNA cassette, containing the gene described in any one of the above items <18> or <21>.
<23> A transformant containing the gene, the recombinant vector, or the DNA cassette described in any one of the above items <18> to <22>.
<24> A method of preparing a transformant containing the steps of introducing the gene, the recombinant vector, or the DNA cassette described in any one of the above items <18> to <22> into a host.
<25> The transformant or the method of preparing the same described in the above items <23> or <24>, wherein the transformant is a transformant of microorganism.
<26> The transformant or the method of preparing the same described in the above item <25>, wherein the microorganism is *Escherichia coli*.
<27> The transformant or the method of preparing the same described in the above item <25>, wherein the microorganism is cyanobacteria.
<28> Use of the protein, the gene, the recombinant vector or the DNA cassette, the transformant, or a transformant obtained by the method of preparing the same described in any one of the above items <15> to <27>, for producing lipids.
<29> The use described in the above item <28>, wherein the fatty acids or lipids contain a medium-chain fatty acid or a fatty acid ester compound thereof, preferably a fatty acid having 8 or more and 10 or less carbon atoms or a fatty acid ester compound thereof, more preferably a fatty acid having 8 or 10 carbon atoms or a fatty acid ester compound thereof, and more preferably a saturated fatty acid having 8 or 10 carbon atoms (caprylic acid, capric acid) or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Tables 1 and 2.

TABLE 1

| Primer Name | Nucleotide Sequence (5'→3') | SEQ ID NO: |
|---|---|---|
| pBS-F | GCGTTAATATTTTGTTAAAATTCGC | 3 |
| pBS-R | AGCTGTTTCCTGTGTGAAATTG | 4 |
| pBS/CpTE-F | ACACAGGAAACAGCTATGGCTAACGGTTCTGCAGTAAC | 5 |
| CpTE/pBS-R | ACAAAATATTAACGCTCAAGTCTTTCCTGTTGATATCGCC | 6 |
| CpTE_T251-R | TAGACCCTTGCGAATGGAATCACC | 7 |
| CpTE_T251R-F | ATTCGCAAGGGTCTACGTCCGGGGTGGTATGACTT | 8 |
| CpTE_T251K-F | ATTCGCAAGGGTCTAAAACCGGGGTGGTATGACTT | 9 |
| CpTE_T251H-F | ATTCGCAAGGGTCTACATCCGGGGTGGTATGACTT | 10 |
| CpTE_W254-R | CCCCGGAGTTAGACCCTTGCG | 11 |
| CpTE_W254I-F | GGTCTAACTCCGGGGATTTATGACTTGGATGTCAA | 12 |
| CpTE_W254Y-F | GGTCTAACTCCGGGGTATTATGACTTGGATGTCAA | 13 |
| CpTE_L257-R | GTCATACCACCCCGGAGTTAGAC | 14 |

TABLE 1-continued

| Primer Name | Nucleotide Sequence (5'→3') | SEQ ID NO: |
|---|---|---|
| CpTE_L257I-F | CCGGGGTGGTATGACATTGATGTCAATCAGCACGT | 15 |
| CpTE_L257M-F | CCGGGGTGGTATGACATGGATGTCAATCAGCACGT | 16 |
| CpTE_L257V-F | CCGGGGTGGTATGACGTTGATGTCAATCAGCACGT | 17 |
| CpTE_L257F-F | CCGGGGTGGTATGACTTTGATGTCAATCAGCACGT | 18 |
| CpTE_V266-R | GTTGCTTACGTGCTGATTGACATCC | 19 |
| CpTE_V266C-F | CAGCACGTAAGCAACTGTAAGTACATTGGGTGGAT | 20 |
| CpTE_W271-R | CCCAATGTACTTCACGTTGCTTACG | 21 |
| CpTE_W271Y-F | GTGAAGTACATTGGGTATATTCTCGAGAGTATGCC | 22 |
| CpTE_V106-R | CGTCTCTATAGAGGCTGTTCGATC | 23 |
| CpTE_V106I-F | GCCTCTATAGAGACGATTATGAACCACGTCCAGGA | 24 |
| CpTE_N108-R | CATCACCGTCTCTATAGAGGCTG | 25 |
| CpTE_N108R-F | ATAGAGACGGTGATGCGTCACGTCCAGGAAACATC | 26 |
| CpTE_N108K-F | ATAGAGACGGTGATGAAACACGTCCAGGAAACATC | 27 |
| CpTE_V110-R | GTGGTTCATCACCGTCTCTATAGAG | 28 |
| CpTE_V110I-F | ACGGTGATGAACCACATTCAGGAAACATCACTCAA | 29 |
| CpTE_V110M-F | ACGGTGATGAACCACATGCAGGAAACATCACTCAA | 30 |
| CpTE_V110L-F | ACGGTGATGAACCACTTACAGGAAACATCACTCAA | 31 |
| CpTE_V110E-F | ACGGTGATGAACCACTTTCAGGAAACATCACTCAA | 32 |
| CpTE_C118-R | TTGATTGAGTGATGTTTCCTGGACG | 33 |
| CpTE_C118I-F | ACATCACTCAATCAAATTAAGAGTATAGGTCTTCT | 34 |
| CpTE_M174-R | ACCGATTTTCCCCGATTGAGAGAGCC | 35 |
| CpTE_M174I-F | TCGGGGAAAATCGGTATTGGTCGCGATTGGCTAAT | 36 |

TABLE 2

| Primer Name | Nucleotide Sequence (5'→3') | SEQ ID NO: |
|---|---|---|
| pUC118/0918up-F | GGATCCTCTAGAGTCAGCTCCGTTGTCGCAGTGTCAG | 37 |
| 0918down/pUC118-R | GCATGCCTGCAGGTCAGACATCACTCAAGTCATCAGTC | 38 |
| 0918up/spr-F | TCGGGCACCACAGGCATCGATTTTCGTTCGTG | 39 |
| spr/0918down-R | AATCGGCTGGGGTTCCATATGCAAGGGTTTATTG | 40 |
| 0918up-R | GCCTGTGGTGCCCGAGGTATAG | 41 |
| 0918down-F | GAACCCCAGCCGATTGAAGATG | 42 |
| Sp-F | ATCGATTTTCGTTCGTG | 43 |
| 0918up/Ptrc-F | TCGGGCACCACAGGCTTGACAATTAATCATCCGGCTCG | 44 |
| Ptrc-R | GGTCTGTTTCCTGTGTGAAATTG | 45 |
| Ptrc/CpTE-F | CACAGGAAACAGACCATGGCTAACGGTTCTGCAGTAAC | 46 |
| CpTE/spr-R | CGAACGAAAATCGATTCAAGTCTTTCCTGTTGATATCGCC | 47 |

Example 1 Lipid Production by *Escherichia coli* into which the CpTE Variant is Introduced (1) Construction of Plasmid for CpTE Gene Expression By using the pBS-SK(−) plasmid (manufactured by Agilent Technologies) as a template, and the primer pBS-F and the primer pBS-R shown in Table 1, PCR was carried out to amplify a linearized DNA sequence of the pBS-SK(−).

Further, TE gene derived from *Cuphea palustris* (Gen-Bank: 038188.1, SEQ ID NO: 49) was artificially synthesized. Using thus-synthesized DNA sequence as a template, and the primer pBS/CpTE-F and the primer CpTE/pBS-R shown in Table 1, PCR was carried out to amplify a fragment of TE gene derived from *Cuphea palustris* (SEQ ID NO: 2, hereinafter, also referred to as "CpTE") wherein sequence of a putative chloroplast transit signal was deleted.

Then, the linearized DNA sequence of the pBS-SK(−) and the fragment of the CpTE gene were mixed to carry out cloning by In-Fusion (registered trademark) PCR cloning method (Clontech), and thereby pBS-CpTE plasmid in which a nucleotide sequence of the CpTE gene was inserted at downstream of lacO promoter of the pBS-SK(−) plasmid was obtained.

(2) Construction of Plasmid for CpTE Variant Gene Expression

By using the pBS-CpTE plasmid as a template, and pairs of any one of the primer CpTE_T251R-F, the primer CpTE_T251K-F and the primer CpTE_T251H-F, and the primer CpTE_T251-R shown in Table 1, PCRs were carried out respectively to obtain gene fragments wherein the nucleotide sequence at positions 751 to 753 of the nucleotide sequence set forth in SEQ ID NO: 2 (nucleotide sequence of CpTE gene) was modified.

Further, by using the pBS-CpTE plasmid as a template, and pairs of any one of the primer CpTE_W254I-F and the primer CpTE_W254Y-F, and the primer CpTE_W254-R shown in Table 1, PCRs were carried out respectively to obtain gene fragments wherein the nucleotide sequence at positions 760 to 762 of the nucleotide sequence set forth in SEQ ID NO: 2 was modified.

Further, by using the pBS-CpTE plasmid as a template, and pairs of any one of the primer CpTE_L257I-F, the primer CpTE_L257M-F, the primer CpTE_L257V-F and the primer CpTE_L257F-F, and the primer CpTE_L257-R shown in Table 1, PCRs were carried out respectively to obtain gene fragments wherein the nucleotide sequence at positions 769 to 771 of the nucleotide sequence set forth in SEQ ID NO: 2 was modified.

Further, by using the pBS-CpTE plasmid as a template, and a pair of the primer CpTE_V266C-F and the primer CpTE_V266-R shown in Table 1, PCR was carried out to obtain a gene fragment wherein the nucleotide sequence at positions 796 to 798 of the nucleotide sequence set forth in SEQ ID NO: 2 was modified.

Further, by using the pBS-CpTE plasmid as a template, and a pair of the primer CpTE_W271Y-F and the primer CpTE_W271-R shown in Table 1, PCR was carried out to obtain a gene fragment wherein the nucleotide sequence at positions 811 to 813 of the nucleotide sequence set forth in SEQ ID NO: 2 was modified.

Furthermore, by using the pBS-CpTE plasmid as a template, and a pair of the primer CpTE_M174I-F and the primer CpTE_M174-R shown in Table 1, PCR was carried out to obtain a gene fragment wherein the nucleotide sequence at positions 520 to 522 of the nucleotide sequence set forth in SEQ ID NO: 2 was modified.

The plasmids for CpTE variant gene expression pBS-CpTE_T251R, pBS-CpTE_T251K, pBS-CpTE_T251H, pBS-CpTE_W254I, pBS-CpTE_W254Y, pBS-CpTE_L257I, pBS-CpTE_L257M, pBS-CpTE pBS-CpTE_L257F, pBS-CpTE_V266C, pBS-CpTE_W271Y, and pBS-CpTE_M174I were constructed respectively by cloning using these gene fragments and In-Fusion (registered trademark) PCR cloning method (Clontech).

In these plasmids, the following nucleotides were substituted for the nucleotides of the nucleotides sequence set forth in SEQ ID NO: 2.

pBS-CpTE_T251R: the nucleotides CGT which encode arginine (R) were substituted for the nucleotides encoding threonine (T) at position 251 of the amino acid sequence set forth in SEQ ID NO: 1.

pBS-CpTE_T251K: the nucleotides AAA which encode lysine (K) were substituted for the nucleotides encoding threonine (T) at position 251 of the amino acid sequence set forth in SEQ ID NO: 1.

pBS-CpTE_T251H: the nucleotides CAT which encode histidine (H) were substituted for the nucleotides encoding threonine (T) at position 251 of the amino acid sequence set forth in SEQ ID NO: 1.

pBS-CpTE_W254I: the nucleotides ATT which encode isoleucine (I) were substituted for the nucleotides encoding tryptophan (W) at position 254 of the amino acid sequence set forth in SEQ ID NO: 1.

pBS-CpTE_W254Y: the nucleotides TAT which encode tyrosine (Y) were substituted for the nucleotides encoding tryptophan (W) at position 254 of the amino acid sequence set forth in SEQ ID NO: 1.

pBS-CpTE_L257I: the nucleotides ATT which encode isoleucine (I) were substituted for the nucleotides encoding leucine (L) at position 257 of the amino acid sequence set forth in SEQ ID NO: 1.

pBS-CpTE_L257M: the nucleotides ATG which encode methionine (M) were substituted for the nucleotides encoding leucine (L) at position 257 of the amino acid sequence set forth in SEQ ID NO: 1.

pBS-CpTE_L257V: the nucleotides GTT which encode valine (V) were substituted for the nucleotides encoding leucine (L) at position 257 of the amino acid sequence set forth in SEQ ID NO: 1.

pBS-CpTE_L257F: the nucleotides TTT which encode phenylalanine (F) were substituted for the nucleotides encoding leucine (L) at position 257 of the amino acid sequence set forth in SEQ ID NO: 1.

pBS-CpTE_V266C: the nucleotides TGT which encode cysteine (C) were substituted for the nucleotides encoding valine (V) at position 266 of the amino acid sequence set forth in SEQ ID NO: 1.

pBS-CpTE_W271Y: the nucleotides TAT which encode tyrosine (Y) were substituted for the nucleotides encoding tryptophan (W) at position 271 of the amino acid sequence set forth in SEQ ID NO: 1.

pBS-CpTE_M174I: the nucleotides ATT which encode isoleucine (I) were substituted for the nucleotides encoding methionine (M) at position 174 of the amino acid sequence set forth in SEQ ID NO: 1.

By using the pBS-CpTE_L257I plasmid as a template, and a pair of the primer CpTE_V106I-F and the primer CpTE_V106-R shown in Table 1, PCR was carried out to obtain a gene fragment wherein the nucleotide sequence at positions 316 to 318 of the nucleotide sequence set forth in SEQ ID NO: 2 was modified, in addition to the nucleotide sequence at positions 769 to 771 thereof.

Further, by using the pBS-CpTE_L257I plasmid as a template, and pairs of any one of the primer CpTE_N108R-and the primer CpTE_N108K-F, and the primer CpTE_N108-R shown in Table 1, PCRs were carried out respectively to obtain gene fragments wherein the nucleotide sequence at positions 322 to 324 of the nucleotide sequence set forth in SEQ ID NO: 2 was modified, in addition to the nucleotide sequence at positions 769 to 771 thereof.

Further, by using the pBS-CpTE_L257I plasmid as a template, and pairs of any one of the primer CpTE_V110I-F, the primer CpTE_V110M-F, the primer CpTE_V110L-F and the primer CpTE_V110E-F, and the primer CpTE_V110-R shown in Table 1, PCRs were carried out respectively to obtain gene fragments wherein the nucleotide sequence at positions 328 to 330 of the nucleotide sequence set forth in SEQ ID NO: 2 was modified, in addition to the nucleotide sequence at positions 769 to 771 thereof.

Furthermore, by using the pBS-CpTE_L257I plasmid as a template, and a pair of the primer CpTE_C118I-F and the primer CpTE_C118-R shown in Table 1, PCR was carried out to obtain a gene fragment wherein the nucleotide sequence at positions 352 to 354 of the nucleotide sequence set forth in SEQ ID NO: 2 was modified, in addition to the nucleotide sequence at positions 769 to 771 thereof.

The plasmids for CpTE variant gene expression pBS-CpTEL257IV106I, pBS-CpTEL257IN108K, pBS-CpTEL257IN108R, pBS-CpTEL257IV110I, pBS-CpTEL257IV110M, pBS-CpTEL257IV110L, pBS-CpTEL257IV110F, and pBS-CpTEL257IC118I were constructed respectively by cloning using these gene fragments and In-Fusion (registered trademark) PCR cloning method (Clontech).

In these plasmids, the following nucleotides were substituted for the nucleotides of the nucleotides sequence set forth in SEQ ID NO: 2.

pBS-CpTEL257IV106I: the nucleotides ATT which encode isoleucine (I) were substituted for the nucleotides encoding leucine (L) at position 257 of the amino acid sequence set forth in SEQ ID NO: 1, and the nucleotides ATT which encode isoleucine (I) were substituted for the nucleotides encoding valine (V) at position 106 thereof.

pBS-CpTEL257IN108K: the nucleotides ATT which encode isoleucine (I) were substituted for the nucleotides encoding leucine (L) at position 257 of the amino acid sequence set forth in SEQ ID NO: 1, and the nucleotides AAA which encode lysine (K) were substituted for the nucleotides encoding asparagine (N) at position 108 thereof.

pBS-CpTEL257IN108R: the nucleotides ATT which encode isoleucine (I) were substituted for the nucleotides encoding leucine (L) at position 257 of the amino acid sequence set forth in SEQ ID NO: 1, and the nucleotides CGT which encode arginine (R) were substituted for the nucleotides encoding asparagine (N) at position 108 thereof.

pBS-CpTEL257IV110I: the nucleotides ATT which encode isoleucine (I) were substituted for the nucleotides encoding leucine (L) at position 257 of the amino acid sequence set forth in SEQ ID NO: 1, and the nucleotides ATT which encode isoleucine (I) were substituted for the nucleotides encoding valine (V) at position 110 thereof.

pBS-CpTEL257IV110M: the nucleotides ATT which encode isoleucine (I) were substituted for the nucleotides encoding leucine (L) at position 257 of the amino acid sequence set forth in SEQ ID NO: 1, and the nucleotides ATG which encode methionine (M) were substituted for the nucleotides encoding valine (V) at position 110 thereof.

pBS-CpTEL257IV110L: the nucleotides ATT which encode isoleucine (I) were substituted for the nucleotides encoding leucine (L) at position 257 of the amino acid sequence set forth in SEQ ID NO: 1, and the nucleotides TTA which encode leucine (L) were substituted for the nucleotides encoding valine (V) at position 110 thereof.

pBS-CpTEL257IV110F: the nucleotides ATT which encode isoleucine (I) were substituted for the nucleotides encoding leucine (L) at position 257 of the amino acid sequence set forth in SEQ ID NO: 1, and the nucleotides TTT which encode phenylalanine (F) were substituted for the nucleotides encoding valine (V) at position 110 thereof.

pBS-CpTEL257IC118I: the nucleotides ATT which encode isoleucine (I) were substituted for the nucleotides encoding leucine (L) at position 257 of the amino acid sequence set forth in SEQ ID NO: 1, and the nucleotides ATT which encode isoleucine (I) were substituted for the nucleotides encoding cysteine (C) at position 118 thereof.

(3) Introduction of Plasmid for Gene Expression into *Escherichia coli*, and Lipid Production Using Thus-Obtained Transformant An *Escherichia coli* mutant strain K27 (fadD88) (Eur. J. Biochem., 1969, vol. 7, 559-574) was transformed by a competent cell transformation method, using the plasmid for the CpTE gene expression and various plasmids for the CpTE variant gene expression. The transformed strain K27 was stand overnight at 30° C., and a colony thus obtained was inoculated in 1 mL of LBAmp liquid medium (Bacto Trypton 1%, Yeast Extract 0.5%, NaCl 1%, and Ampicillin sodium 50 μg/mL), and then cultured overnight at 30° C. The culture fluid of 2 μL was inoculated to 2 mL of Overnight Express Instant TB Medium (Novagen) and was subjected to shaking culture at 30° C. After 24 hours cultivation, lipid components contained in the culture fluid were analyzed by the method described below.

(4) Extraction of Lipid from *Escherichia coli* Culture Fluid and Analysis of Fatty Acids Contained Therein To 1 mL of the culture fluid, 25 μL of 1 mg/mL 7-pentadecanone as an internal standard was added, and then 10 μL of 2N hydrochloric acid and 2 mL of hexane were further added. The mixture was vigorously stirred and centrifuged for 10 minutes at 3,000 rpm. Then the hexane layer (upper layer) was collected with pasteur pipette into a test tube with screw cap.

A nitrogen gas was blown onto the resultant hexane layer to be dried into solid, then 1 mL of 14% solution of boron trifluoride (manufactured by Sigma-Aldrich) was added to the sample, and the mixture was kept warm at 80° C. for 30 minutes. Thereafter, 1 mL of saturated saline and 1 mL of hexane were added thereto, and the mixture was vigorously stirred and then was left for 30 minutes at room temperature. Then, the hexane layer being upper layer was collected to obtain fatty acid esters.

The obtained fatty acid esters were provided for gas chromatographic analysis. Using 7890A (Agilent Technologies), gas chromatographic analysis was performed under the conditions as follows.

(Analysis Conditions)
Capillary column: DB-1 MS (30 m×200 μm×0.25 μm, manufactured by J&W Scientific)
Mobile phase: high purity helium
Flow rate inside the column: 1.0 mL/min
Temperature rise program: maintained for 1 minute at 70° C.→70 to 200° C. (temperature increase at 20° C./minute)→200 to 320° C. (temperature increase at 50° C./minute)→maintained for 5 minutes at 320° C.
Equilibration time: 1 min
Injection port: split injection (split ratio: 100:1)
Pressure: 14.49 psi, 104 mL/min Amount of injection: 1 μL
Cleaning vial: methanol/chloroform
Detector temperature: 300° C.

The fatty acid esters were identified by providing the identical sample for gas chromatography—mass spectrometry analysis under identical conditions described above.

Amounts of the fatty acid methyl esters were quantitatively determined based on the peak areas of waveform data obtained by the above gas chromatographic analysis. The peak area was compared with that of 7-pentadecanone as the internal standard, and corrections between the samples were carried out, and then the amount of each of the fatty acids and the total amount thereof per liter of the culture fluid were calculated.

Further, the amount of C8 fatty acid and C10 fatty acid in the transformant into which wild-type CpTE gene or L257I gene were introduced were taken as 1 for each, and the amount of C8 fatty acid and C10 fatty acid in the transformant into which the CpTE variant gene was introduced were calculated for each in terms of a relative value.

Tables 3 and 4 show the results. In addition, the results in Tables 3 and 4 are shown in terms of an average value of the results of independent culture three times and chromatography analyses thereof.

TABLE 3

|  | Wild Type | T251R | T251K | T251H | W254I | W254Y |
|---|---|---|---|---|---|---|
| C8 Fatty Acid | 1.00 | 1.96 | 1.36 | 1.81 | 2.32 | 1.46 |
| C10 Fatty Acid | 1.00 | 2.41 | 1.58 | 2.23 | 3.17 | 1.68 |

|  | L257I | L257M | L257V | L257F | V266C | W271Y |
|---|---|---|---|---|---|---|
| C8 Fatty Acid | 6.80 | 2.10 | 3.58 | 1.55 | 1.37 | 3.09 |
| C10 Fatty Acid | 10.06 | 2.33 | 3.10 | 1.53 | 1.57 | 4.04 |

TABLE 4

|  | L257I | L257I + V106I | L257I + N108K | L257I + N108R | L257I + V110I | L257I + V110M | L257I + V110L | L257I + V110F | L257I + C118I |
|---|---|---|---|---|---|---|---|---|---|
| C8 Fatty Acid | 1.00 | 1.40 | 1.32 | 1.20 | 1.18 | 1.52 | 1.76 | 1.75 | 1.21 |
| C10 Fatty Acid | 1.00 | 1.17 | 1.24 | 1.37 | 0.94 | 1.45 | 1.74 | 2.15 | 0.42 |

As is apparent from Table 3, production amounts of both C8 fatty acid and C10 fatty acid were highly increased in the transformant into which the CpTE variant gene of the present invention was introduced, in comparison with the production amounts of C8 fatty acid and C10 fatty acid in the transformant into which the wild-type CpTE gene was introduced to express the wild-type CpTE.

Specifically, production amount of C8 fatty acid was increased respectively by 1.96 times in a case where the T251R gene was introduced, by 1.36 times in a case where the T251K gene was introduced, by 1.81 times in a case where the T251H gene was introduced, by 2.32 times in a case where the W254I gene was introduced, by 1.46 times in a case where the W254Y gene was introduced, by 6.80 times in a case where the L257I gene was introduced, by 2.10 times in a case where the L257M gene was introduced, by 3.58 times in a case where the L257V gene was introduced, by 1.55 times in a case where the L257F gene was introduced, by 1.37 times in a case where the V266C gene was introduced, and by 3.09 times in a case where the W271Y gene was introduced, compared with a case where wild-type CpTE gene was introduced.

Further, production amount of C10 fatty acid was increased respectively by 2.41 times in a case where the T251R gene was introduced, by 1.58 times in a case where the T251K gene was introduced, by 2.23 times in a case where the T251H gene was introduced, by 3.17 times in a case where the W254I gene was introduced, by 1.68 times in a case where the W254Y gene was introduced, by 10.06 times in a case where the L257I gene was introduced, by 2.23 times in a case where the L257M gene was introduced, by 3.10 times in a case where the L257V gene was introduced, by 1.53 times in a case where the L257F gene was introduced, by 1.57 times in a case where the V266C gene was introduced, and by 4.04 times in a case where the W271Y gene was introduced, compared with a case where wild-type CpTE gene was introduced.

Further as is apparent from Table 4, by providing at least one amino acid substitution selected from the group consisting of the (D-1) to (D-8) with CpTE(L257I) which significantly increased of production amounts of C8 fatty acid and C10 fatty acid, production amounts of C8 fatty acid and C10 fatty acid were further increased.

Specifically, production amount of C8 fatty acid was increased respectively by 1.40 times in a case where the L257IV106I gene was introduced, by 1.32 times in a case where the L257I N108K gene was introduced, by 1.20 times in a case where the L257IN108R gene was introduced, by 1.18 times in a case where the L257IV110I gene was introduced, by 1.52 times in a case where the L257IV110M gene was introduced, by 1.76 times in a case where the L257IV110L gene was introduced, by 1.75 times in a case where the L257IV110F gene was introduced, and by 1.21 times in a case where the L257I C118I gene was introduced, compared with a case where the L257I gene was introduced.

Further, production amount of C10 fatty acid was increased respectively by 1.17 times in a case where the L257IV106I gene was introduced, by 1.24 times in a case where the L257IN108K gene was introduced, by 1.37 times in a case where the L257I N108R gene was introduced, by 1.45 times in a case where the L257IV110M gene was introduced, by 1.74 times in a case where the L257IV110L gene was introduced, and by 2.15 times in a case where the L257IV110F gene was introduced, compared with a case where the L257I gene was introduced.

As described above, when *Escherichia coli* is used as the host of the transformant, the transformant in which the productivity of medium-chain fatty acids is significantly improved can be prepared by using the CpTE variant into which amino acid mutation specified in the present invention is introduced. Then, the productivity of medium-chain fatty acids can be improved by culturing the transformant.

Further, amount of C8 fatty acid and amount of C10 fatty acid of the transformant were taken as 1, respectively, with regard to the transformant into which the gene encoding CpTE_M174I (CpTE variant in which isoleucine (I) is substituted for methionine (M) at position 174 of the amino acid sequence set forth in SEQ ID NO: 1) disclosed in Patent Literature 3 (US 2011/0020883) was introduced, and amount of C8 fatty acid and amount of C10 fatty acid of the transformant into which the L257I gene was introduced were calculated as a relative value, respectively. The results are shown in Table 5.

TABLE 5

|  | M174I (reference example, see Patent literature 3) | L257I |
|---|---|---|
| C8 Fatty Acid | 1.00 | 1.78 |
| C10 Fatty Acid | 1.00 | 2.25 |

Patent Literature 3 describes that production amount of C8 fatty acid is improved in the transformant into which the CpTE_M174I gene is introduced. As is apparent from Table 5, even in comparison with such a transformant, when the CpTE_L257I gene was introduced, production amount of C8 fatty acid was improved by 1.78 times. Further, production amount of C10 fatty acid was also increased by 2.25 times.

From the results, the transformant into which the CpTE_L257I gene is introduced is particularly effective in producing C8 fatty acid and C10 fatty acid.

Example 2 Lipid Production by Cyanobacteria into which CpTE Variant is Introduced (1) Inactivation of aas Gene and Construction of Plasmid for CpTE Variant Gene Expression By using genomic DNA of wild-type strain of *Synechococcus elonqatus* sp. strain PCC7942, and the primer pUC118/0918up-F and the primer 0918down/pUC118-R shown in Table 2, PCR was carried out to amplify a fragment (2864 bp, SEQ ID NO: 50) containing a Synpcc7942_0918 gene (aas gene). The amplified fragment was inserted into a place between HincII sites of a pUC118 plasmid (manufactured by Takara Bio) by applying an In-Fusion (registered trademark) PCR Cloning method (Clontech) to prepare a pUC118-Synpcc7942_0918 plasmid into which the Synpcc7942_0918 gene (aas gene) was incorporated.

A pDG1726 plasmid (Gene, 1995, vol. 167, p. 335-336) was used as a template, and PCR was carried out by using the primer 0918up/spr-F (SEQ ID NO:) and the primer spr/0918down-R (SEQ ID NO:) shown in Table 2 to obtain a spectinomycin resistance marker gene (SEQ ID NO: 51) fragment (hereinafter, also referred to as "sp fragment").

Next, the pUC118-Synpcc7942_0918 plasmid was used as a template, and PCR was carried out by using the primer 0918up-R and the primer 0918down-F shown in Table 2 to obtain a linearized DNA fragment in which a 927 bp region between coding regions of the Synpcc7942_0918 gene (aas gene) was deleted.

The linearized DNA fragment and the sp fragment were bonded by applying the In-Fusion (registered trademark) PCR Cloning method (Clontech) to obtain a pUC118-Synpcc7942_0918::sp plasmid containing a DNA sequence of the coding region of the Synpcc7942_0918 gene into which the sp fragment was inserted.

The pUC118-Synpcc7942_0918::sp plasmid was used as a template, and PCR was carried out by using the primers 0918up-R and Sp-F shown in Table 2 to linearize the pUC118-Synpcc7942_0918::sp plasmid.

Next, using the trc promoter sequence which was artificially synthesized from pTrc99A cloning plasmid (NCBI Accession number: M22744) sequence as a template, and the primer 0918up/Ptrc-F and the primer Ptrc-R shown in Table 2, PCR was carried out to amplify a trc promoter fragment (Ptrc fragment, SEQ ID NO: 52).

Using the DNA sequence of the TE gene derived from *Cuphea palustris* (GenBank: U38188.1) which was artificially synthesized in Example 1 as a template, and a pair of the primers Ptrc/CpTE-F and CpTE/spr-R shown in Table 2, PCR was carried out to amplify a fragment of the TE gene (CpTE gene) derived from *Cuphea palustris* wherein putative chloroplast transit signal sequence was deleted.

Then, the linearized pUC118-Synpcc7942_0918::sp plasmid, the Ptrc fragment and the fragment of the CpTE gene were mixed, and the resultant mixture was cloned by the In-Fusion (registered trademark) PCR Cloning method (Clontech) to obtain a pUC118-Synpcc7942_0918::Ptrc-CpTE-sp plasmid in which the Ptrc fragment, the CpTE gene fragment and the sp fragment were inserted into a place between the coding regions of the Synpcc7942_0918 gene in this order.

(2) Construction of Plasmid for CpTE Variant Gene Expression

Using the pBS-CpTE plasmid prepared in Example 1 as a template, and a pair of the primers CpTE_L257I-F and CpTE_L257-R shown in Table 1, PCR was carried out to obtain a gene fragment of pBS-CpTE_L257I wherein the nucleotide sequence at positions 769 to 771 of the nucleotide sequence set forth in SEQ ID NO: 2 was modified.

Using thus-obtained gene fragment and the pUC118-Synpcc7942_0918::Ptrc-CpTE-sp plasmid, cloning was carried out by applying the In-Fusion (registered trademark) PCR cloning method (Clontech), and thereby a plasmid for CpTE variant gene expression pUC118-Synpcc7942_0918::Ptrc-CpTE_L257I-sp was obtained.

In the gene fragment pBS-CpTE_L257I, the following nucleotides were substituted for the nucleotides of the nucleotide sequence set forth in SEQ ID NO: 2.

pBS-CpTE_L257I: the nucleotides ATT which encode isoleucine (I) were substituted for the nucleotides encoding leucine (L) at position 257 of the amino acid sequence set forth in SEQ ID NO: 1

(3) Introduction of Plasmid for Gene Expression into Cyanobacteria, and Lipid Production by Using Thus-Obtained Transformant The *Synechococcus elonqatus* sp. strain PCC7942 was transformed by using the plasmid for the CpTE gene expression or the plasmid for the CpTE variant gene expression by the spontaneous transformation method, and the strain into which the desired gene was introduced was selected by spectinomycin resistance.

Thus, Δ0918::CpTE strain and Δ0918::CpTE_L257I strain were obtained respectively, wherein a construct for CpTE gene expression or CpTE variant expression was introduced into the aas region on a genome of strain *Synechococcus elonqatus* sp. PCC7942.

In a 50 mL Erlenmeyer flask to which 25 mL of BG-11 medium having the composition shown in Table 6 below was added, the transformant was cultured for two weeks by setting an initial bacterial cell concentration to 0.2 in $OD_{730}$ by using a rotary shaker (120 rpm) at 30° C. under predetermined lighting (60 $\mu E \cdot m^{-2} \cdot sec^{-1}$). In addition, spectinomycin was added to the BG-11 medium to be 25 μg/mL in a concentration.

TABLE 6

Composition of BG-11 liquid medium

Stock solution

| | |
|---|---|
| A solution | 2 mL |
| B solution | 50 mL |
| C solution | 2 mL |
| D solution | 1 mL |
| E solution | 1 mL |
| 1.0M TES-KOH (pH 7.5) | 10 mL |
| Total | 1000 mL |

Composition of stock solution

| A solution | | B solution | |
|---|---|---|---|
| Citric acid•H$_2$O | 0.33 g | NaNO$_3$ | 30 g |
| Ferric ammonium citrate | 0.3 g | K$_2$HPO$_4$ | 0.78 g |
| Na$_2$EDTA | 0.05 g | MgSO$_4$•7H$_2$O | 1.5 g |
| total | 100 mL | total | 100 mL |

C solution CaCl$_2$•2H$_2$O 1.9 g/100 mL
D solution
[H$_3$BO$_3$ 2.86 g, MnCl$_2$•4H$_2$O 1.81 g, ZnSO$_4$•7H$_2$O 0.22 g, CuSO$_4$•5H$_2$O 0.08 g, Na$_2$MoO$_4$ 0.021 g, Co (NO$_3$)•6H$_2$O 0.0494 g, H$_2$SO$_4$ single drop]/1000

After completion of the culture, 1 g of NaH$_2$PO$_4$ and 25 μL of 7-pentadecanone (1 mg/mL) as an internal standard were added to 25 mL of culture fluid. Then, 10 mL of hexane was added to this fluid, and the resultant mixture was sufficiently stirred and then left to stand for 10 minutes. The resultant mixture was centrifuged at 2,500 rpm for 10 minutes at room temperature, and then an upper layer portion was collected in an eggplant flask. Then, 5 mL of hexane was further added to a lower layer obtained by centrifugation, and the resultant mixture was stirred, centrifuged twice and concentrated in vacuum to obtain a dried sample.

1 mL of 14% solution of boron trifluoride (manufactured by Sigma-Aldrich) was added to the dried sample, and the mixture was kept warm at 80° C. for 30 minutes. Thereafter, 1 mL of hexane and 1 mL of saturated saline were added thereto, and the mixture was vigorously stirred and then was left for 30 minutes at room temperature. Then, the hexane layer being upper layer was collected to obtain fatty acid methyl esters.

The obtained fatty acid methyl esters were provided for gas chromatographic analysis by a method similar to that in Example 1. The results are shown in Table 7. In addition, the results in Table 7 are shown in terms of an average value of the results of independent culture three times and chromatography analyses thereof.

TABLE 7

| | Wild Type | L257I |
|---|---|---|
| C8 Fatty Acid | 1.00 | 2.97 |
| C10 Fatty Acid | 1.00 | 5.10 |

As shown in Table 7, in comparison with production amount of C8 fatty acid and production amount of C10 fatty acid in the transformant into which the wild-type CpTE gene was introduced, production amount of C8 fatty acid and production amount of C10 fatty acid were both significantly increased by 2.97 times and 5.10 times, respectively, in the transformant into which the CpTE variant gene of the present invention was introduced.

As described above, when cyanobacteria is used as the host of the transformant, the transformant in which the productivity of medium-chain fatty acids is significantly improved can be prepared by using the CpTE variant into which amino acid mutation specified according to the present invention is introduced. Then, the productivity of medium-chain fatty acids can be improved by culturing this transformant.

As described above, the transformant in which productivity of medium-chain fatty acids was improved can be prepared by introducing a gene encoding the TE variant gene specified in the present invention into a host. Then, the productivity of medium-chain fatty acids a can be improved by culturing this transformant.

Having described our invention as related to the present embodiments, it is our intention that the invention not be limited by any of the details of the description, unless otherwise specified, but rather be construed broadly within its spirit and scope.

This application claims priority on Patent Application No. 2017-196237 filed in Japan on Oct. 6, 2017, which is entirely herein incorporated by reference.

The invention claimed is:

1. A method of producing fatty acids or lipids, comprising the steps of: culturing a transformant into which a gene encoding at least one protein selected from the group consisting of the following proteins (A), (B), and (C) is introduced and expressed; and producing fatty acids or lipids containing the same as components during the culturing; wherein protein (A) is: (A) a protein, the amino acid sequence of which consists of the amino acid sequence of SEQ ID NO:1 except that the protein's amino acid sequence has at least one amino acid substitution selected from the following (A-1) to (A-11) as compared to the amino acid sequence of SEQ ID NO: 1, and having acyl-ACP thioesterase activity; wherein protein (B) is: (B) a protein, the amino acid sequence of which consists of an amino acid sequence that has 85% or more sequence identity to SEQ ID NO:1, and in which there is at least one amino acid substitution selected from the following (B-1) to (B-11) as compared to the amino acid sequence of the protein that has 85% or more identity with the amino acid sequence of SEQ ID NO: 1, and having acyl-ACP thioesterase activity; and wherein protein (C) is: (C) a protein, the amino acid sequence of which comprises the amino acid sequence of protein (A) or (B), and having acyl-ACP thioesterase activity; wherein substitutions (A-1) to (A-11) are:
(A-1) substitution of isoleucine for leucine at position 257 of the amino acid sequence set forth in SEQ ID NO: 1;
(A-2) substitution of arginine for threonine at position 251 of the amino acid sequence set forth in SEQ ID NO: 1;
(A-3) substitution of lysine for threonine at position 251 of the amino acid sequence set forth in SEQ ID NO: 1;
(A-4) substitution of histidine for threonine at position 251 of the amino acid sequence set forth in SEQ ID NO: 1;
(A-5) substitution of isoleucine for tryptophan at position 254 of the amino acid sequence set forth in SEQ ID NO: 1;
(A-6) substitution of tyrosine for tryptophan at position 254 of the amino acid sequence set forth in SEQ ID NO: 1;
(A-7) substitution of methionine for leucine at position 257 of the amino acid sequence set forth in SEQ ID NO: 1;
(A-8) substitution of valine for leucine at position 257 of the amino acid sequence set forth in SEQ ID NO: 1;
(A-9) substitution of phenylalanine for leucine at position 257 of the amino acid sequence set forth in SEQ ID NO: 1;
(A-10) substitution of cysteine for valine at position 266 of the amino acid sequence set forth in SEQ ID NO: 1;
(A-11) substitution of tyrosine for tryptophan at position 271 of the amino acid sequence set forth in SEQ ID NO: 1;
wherein substitutions (B-1) to (B-11) are:
(B-1) substitution of isoleucine for an amino acid at a position corresponding to position 257 of the amino acid sequence set forth in SEQ ID NO: 1;
(B-2) substitution of arginine for an amino acid at a position corresponding to position 251 of the amino acid sequence set forth in SEQ ID NO: 1;
(B-3) substitution of lysine for an amino acid at a position corresponding to position 251 of the amino acid sequence set forth in SEQ ID NO: 1;
(B-4) substitution of histidine for an amino acid at a position corresponding to position 251 of the amino acid sequence set forth in SEQ ID NO: 1;
(B-5) substitution of isoleucine for an amino acid at a position corresponding to position 254 of the amino acid sequence set forth in SEQ ID NO: 1;
(B-6) substitution of tyrosine for an amino acid at a position corresponding to position 254 of the amino acid sequence set forth in SEQ ID NO: 1;
(B-7) substitution of methionine for an amino acid at a position corresponding to position 257 of the amino acid sequence set forth in SEQ ID NO: 1;
(B-8) substitution of valine for an amino acid at a position corresponding to position 257 of the amino acid sequence set forth in SEQ ID NO: 1;
(B-9) substitution of phenylalanine for an amino acid at a position corresponding to position 257 of the amino acid sequence set forth in SEQ ID NO: 1;
(B-10) substitution of cysteine for an amino acid at a position corresponding to position 266 of the amino acid sequence set forth in SEQ ID NO: 1; and
(B-11) substitution of tyrosine for an amino acid at a position corresponding to position 271 of the amino acid sequence set forth in SEQ ID NO: 1.

2. The method of claim 1, wherein the culturing improves the transformant's productivity of medium-chain fatty acids having 8 or 10 carbon atoms or lipids containing the same as compared to the productivity of the transformant's host that has not been transformed with the gene encoding the at least one protein selected from the group consisting of proteins (A), (B), and (c).

3. The method of claim 1, wherein the culturing increases the proportion of medium-chain fatty acids having 8 or 10 carbon atoms that are in the total fatty acid composition produced by the transformant as compared to the proportion produced by the transformant's host that has not been transformed with a gene encoding the at least one protein selected from the group consisting of proteins (A), (B), and (C).

4. The method of claim 2, wherein protein (A) also has at least one amino acid substitution selected from the following (D-1) to (D-8), and protein (B) also has at least one amino acid substitution selected from the following (E-1) to (E-8); wherein substitutions (D-1) to (D-8) are:
(D-1) substitution of isoleucine for valine at position 106 of the amino acid sequence set forth in SEQ ID NO: 1;
(D-2) substitution of lysine for asparagine at position 108 of the amino acid sequence set forth in SEQ ID NO: 1;
(D-3) substitution of arginine for asparagine at position 108 of the amino acid sequence set forth in SEQ ID NO: 1;
(D-4) substitution of isoleucine for valine at position 110 of the amino acid sequence set forth in SEQ ID NO: 1;
(D-5) substitution of methionine for valine at position 110 of the amino acid sequence set forth in SEQ ID NO: 1;
(D-6) substitution of leucine for valine at position 110 of the amino acid sequence set forth in SEQ ID NO: 1;
(D-7) substitution of phenylalanine for valine at position 110 of the amino acid sequence set forth in SEQ ID NO: 1;
(D-8) substitution of isoleucine for cysteine at position 118 of the amino acid sequence set forth in SEQ ID NO: 1;
wherein substitutions (E-1) to (E-8) are:
(E-1) substitution of isoleucine for an amino acid at a position corresponding to position 106 of the amino acid sequence set forth in SEQ ID NO: 1;
(E-2) substitution of lysine for an amino acid at a position corresponding to position 108 of the amino acid sequence set forth in SEQ ID NO: 1;

(E-3) substitution of arginine for an amino acid at a position corresponding to position 108 of the amino acid sequence set forth in SEQ ID NO: 1;
(E-4) substitution of isoleucine for an amino acid at a position corresponding to position 110 of the amino acid sequence set forth in SEQ ID NO: 1;
(E-5) substitution of methionine for an amino acid at a position corresponding to position 110 of the amino acid sequence set forth in SEQ ID NO: 1;
(E-6) substitution of leucine for an amino acid at a position corresponding to position 110 of the amino acid sequence set forth in SEQ ID NO: 1;
(E-7) substitution of phenylalanine for an amino acid at a position corresponding to position 110 of the amino acid sequence set forth in SEQ ID NO: 1; and
(E-8) substitution of isoleucine for an amino acid at a position corresponding to position 118 of the amino acid sequence set forth in SEQ ID NO: 1.

5. The method of claim 4, wherein protein (A) has the amino acid substitution of (A-1) and at least one amino acid substitution selected from (D-1) to (D-8), and protein (B) has the amino acid substitution of (B-1) and at least one amino acid substitution selected from (E-1) to (E-8).

6. The method of claim 2, wherein the transformant is a microorganism.

7. The method of claim 6, wherein the microorganism is *Escherichia coli*.

8. The method of claim 6, wherein the microorganism is a cyanobacteria.

9. The method of claim 1, wherein the fatty acids or lipids contain a medium-chain fatty acid having 8 or 10 carbon atoms or a fatty acid ester compound thereof.

* * * * *